(12) United States Patent
Shin et al.

(10) Patent No.: US 10,604,775 B2
(45) Date of Patent: Mar. 31, 2020

(54) CANDIDA INFANTICOLA STRAIN, MUTANT STRAIN AND TRANSFORMANT STRAIN THEREOF, AND METHOD FOR PRODUCING DIOIC ACIDS USING SAME

(71) Applicant: LOTTE CHEMICAL CORPORATION, Songpa-gu, Seoul (KR)

(72) Inventors: Dong Myung Shin, Yuseong-gu (KR); Jong Pill Kim, Yuseong-gu (KR); Heejoon Park, Yuseong-gu (KR); Seung Hoon Lee, Yuseong-gu (KR); Hye Ran Jang, Eunpyeong-gu (KR); Hongweon Lee, Cheongju-si (KR); Jung Oh Ahn, Cheongju-si (KR); Woo Young Jeon, Cheongju-si (KR); Gyu Yeon Park, Cheongju-si (KR); Hee Suk Lee, Cheongju-si (KR)

(73) Assignee: LOTTE CHEMICAL CORPORATION, Seoul (KR)

( * ) Notice: Subject to any disclaimer, the term of this patent is extended or adjusted under 35 U.S.C. 154(b) by 0 days.

(21) Appl. No.: 15/762,294

(22) PCT Filed: Sep. 23, 2016

(86) PCT No.: PCT/KR2016/010706
§ 371 (c)(1),
(2) Date: Mar. 22, 2018

(87) PCT Pub. No.: WO2017/052299
PCT Pub. Date: Mar. 30, 2017

(65) Prior Publication Data
US 2019/0040422 A1  Feb. 7, 2019

(30) Foreign Application Priority Data

Sep. 23, 2015 (KR) .................. 10-2015-0134598
Sep. 22, 2016 (KR) .................. 10-2016-0121723
Sep. 22, 2016 (KR) .................. 10-2016-0121725

(51) Int. Cl.
| | | |
|---|---|---|
| C12N 1/20 | (2006.01) | |
| C12P 7/44 | (2006.01) | |
| C12P 7/64 | (2006.01) | |
| C12P 1/02 | (2006.01) | |
| C12N 1/14 | (2006.01) | |
| C12N 9/02 | (2006.01) | |
| C12R 1/72 | (2006.01) | |

(52) U.S. Cl.
CPC .................. *C12P 7/44* (2013.01); *C12N 1/14* (2013.01); *C12N 9/001* (2013.01); *C12P 1/02* (2013.01); *C12P 7/64* (2013.01); *C12Y 103/03006* (2013.01); *C12R 1/72* (2013.01)

(58) Field of Classification Search
CPC .................................. C12N 9/001; C12P 7/64
USPC ............................................. 435/134, 254.22
See application file for complete search history.

(56) References Cited

U.S. PATENT DOCUMENTS

| | | | |
|---|---|---|---|
| 3,843,466 | A | 10/1974 | Uchio et al. |
| 4,925,798 | A | 5/1990 | Hill |
| 2010/0285545 | A1 | 11/2010 | Gross et al. |
| 2015/0044739 | A1 | 2/2015 | Liu et al. |

FOREIGN PATENT DOCUMENTS

| | | |
|---|---|---|
| JP | 2009-521918 A | 6/2009 |
| JP | 2014-201554 A | 10/2014 |
| KR | 10-0221504 B1 | 9/1999 |
| KR | 10-2015-0078989 A | 7/2015 |
| WO | WO 2007/096654 A2 | 8/2007 |

OTHER PUBLICATIONS

Kurtzman [Antonie van Leeuwenhoek (2007) 92:221-231], 2007.*
International Search Report for International application No. PCT/KR2016/010706, dated Dec. 8, 2016, in 4 pages.
Kurtzman, "New anamorphic yeast species: *Candida infanticola* sp. nov., *Candida polysorbophila* sp. nov., *Candida transvaalensis* sp. nov. and *Trigonopsis californica* sp. nov.", Antonie Van Leeuwenhoek, 2007, vol. 92, pp. 221-231.
Lee, et al., "Characterization of the newly isolated ω-oxidizing yeast *Candida sorbophila* DS02 and its potential applications in long-chain dicarboxylic acid production", Appl Microbiol Biotechnol, 2017, vol. 101, pp. 6333-6342.

\* cited by examiner

*Primary Examiner* — Tekchand Saidha
(74) *Attorney, Agent, or Firm* — Knobbe, Martens, Olson & Bear, LLP

(57) ABSTRACT

The present invention relates to a method for producing dioic acids from a substrate containing hydrocarbons or fatty acids using a *Candida infanticola* strain, and to a *Candida infanticola* microorganism used therefor. The present invention reduces the cost increase resulting from the fluctuation in the international oil price and the burden of environmental pollution, which are caused by the use of fossil fuels, and thus can be utilized in various industrial fields using DDDA as a raw material.

5 Claims, 21 Drawing Sheets
Specification includes a Sequence Listing.

Fig. 4

```
tccgtaggtg aacctgcgga aggatcatta ttgagattca tattacacct gtgaaacaac    60
taaattgctt ggccgaaagg ccaatgtaac aaaaactatt ttacctatta tatctgaaaa   120
acgaaatcaa aagtttcaac aacggatctc ttggttctcg catcgatgaa gaacgcagca   180
aagcgcgata gttagtgtga attgcagacg tgaatcattg agttttgaa cgcacattgc    240 accttctggt attccgggaa gtatacttgt gcgagcgtca tttcatcttc ataaagcaat   300
ttatgtgttg gggctgtagc cagccttgaa aaagatgata gagtacatgt tagacacaat   360
gtgcttttct atatttttga cctcgtatca agcaagatta cccgctgaac ttaagcatat   420
caataagcgg agga                                                     434
```

Δpox2 mutant colony PCR

CANDIDA INFANTICOLA STRAIN, MUTANT STRAIN AND TRANSFORMANT STRAIN THEREOF, AND METHOD FOR PRODUCING DIOIC ACIDS USING SAME

REFERENCE TO THE SEQUENCE LISTING

A Sequence Listing submitted as an ASCII text file via EFS-Web is hereby incorporated by reference in accordance with 35 U.S.C. § 1.52(e). The Sequence Listing is provided as a file entitled TERA001.001APC.txt, created Aug. 7, 2018, which is 19 KB in size.

TECHNICAL FIELD

The present invention relates to a method for producing dioic acids from a substrate containing hydrocarbons or fatty acids using *Candida infanticola* strain and *Candida infanticola* microorganism used therefor.

BACKGROUND ART

Dioic acids are very important chemicals in the chemical industry, and used for a variety of industrial applications such as not only petroleum-derived nylon used in engineering resins, automobile parts, sporting goods, carpets and toothbrushes but also other polymeric plasticizers, adhesives, lubricants, epoxy resins, corrosion inhibitors, coating agents, processed plastic, perfumes and pharmaceutical products. Of these dioic acids, about 15,000,000,000 pounds of dodecanedioic acids are synthesized from petrochemical raw materials annually. These petrochemical raw materials are mainly scarce natural raw materials, and their use is closely related to environmental destruction and change around the world, and these petrochemical raw materials are sensitive to price fluctuations and increase the burden on environmental pollution.

Accordingly, there is a need for alternative production methods of dioic acids that are renewable, sustainable and able to reduce the burden on the environment.

DISCLOSURE

Technical Problem

In order to solve the above problems in the art, an object of the present invention is to provide a method for producing dioic acids and *Candida infanticola* strain.

Technical Solution

In order to achieve the above object, the present invention provides a method for producing dioic acids from a substrate containing hydrocarbons or fatty acids using *Candida infanticola* strain.

The method for producing dioic acids may comprise the following steps of:

(A) culturing *Candida infanticola* strain in yeast extract glucose medium (YG medium) supplemented with a substrate containing hydrocarbons or fatty acids for securing initial cell mass;

(B) adding a carbon source or a substrate containing hydrocarbons, fatty acids or its derivatives to the culture solution obtained in the step (A) to induce ω-oxidation reaction; and (C) culturing the reaction solution obtained in the step (B) while adding a substrate containing hydrocarbons or fatty acids and glucose.

The culture of the step (A) may be conducted at a condition of 30±5° C., dissolved oxygen of 10% or more for 20 hours to 50 hours.

Further, the reaction of the step (B) may be conducted with a carbon source of 0.5% to 5% for 10 hours to 30 hours.

Further, the culture of the step (C) is conducted with the substrate of 0.1 ml/L/h to 2 ml/L/h and the glucose of 1 g/L/h to 3 g/L/h for 50 hours to 100 hours.

In the method for producing dioic acids, the dioic acids may be selected from the group consisting of ethanedioic acid, propanedioic acid, butanedioic acid, pentanedioic acid, hexanedioic acid, octanedioic acid, nonanedioic acid, decanedioic acid, undecanedioic acid, dodecanedioic acid, hexadecanedioic acid and a combination thereof.

In the method for producing dioic acids, the *Candida infanticola* strain may be *Candida infanticola* wild type strain (*Candida infanticola* DS02; KCTC 12820BP), *Candida infanticola* mutant strain (*Candida infanticola* LC-DA01; KCTC13099BP), *Candida infanticola* transformant strain (*Candida infanticola*; KCTC13103BP, KCTC13104BP, KCTC13105BP, KCTC13106BP) or a combination thereof.

Further, the present invention provides *Candida infanticola* strain producing dioic acids from a substrate containing hydrocarbons or fatty acids.

Advantageous Effects

The present invention relates to a method for producing dioic acids from a substrate containing hydrocarbons or fatty acids using a *Candida infanticola* strain, and to a *Candida infanticola* microorganism used therefor. The present invention reduces the cost increase resulting from the fluctuation in the international oil price and the burden of environmental pollution, which are caused by the use of fossil fuels, and thus can be utilized in various industrial fields using DDDA as a raw material.

DESCRIPTION OF DRAWINGS

FIG. 4 is a drawing showing 18s rRNA base sequence (SEQ ID NO: 1) of an isolated strain.

DEPOSIT OF MICROORGANISM

Figure 1:
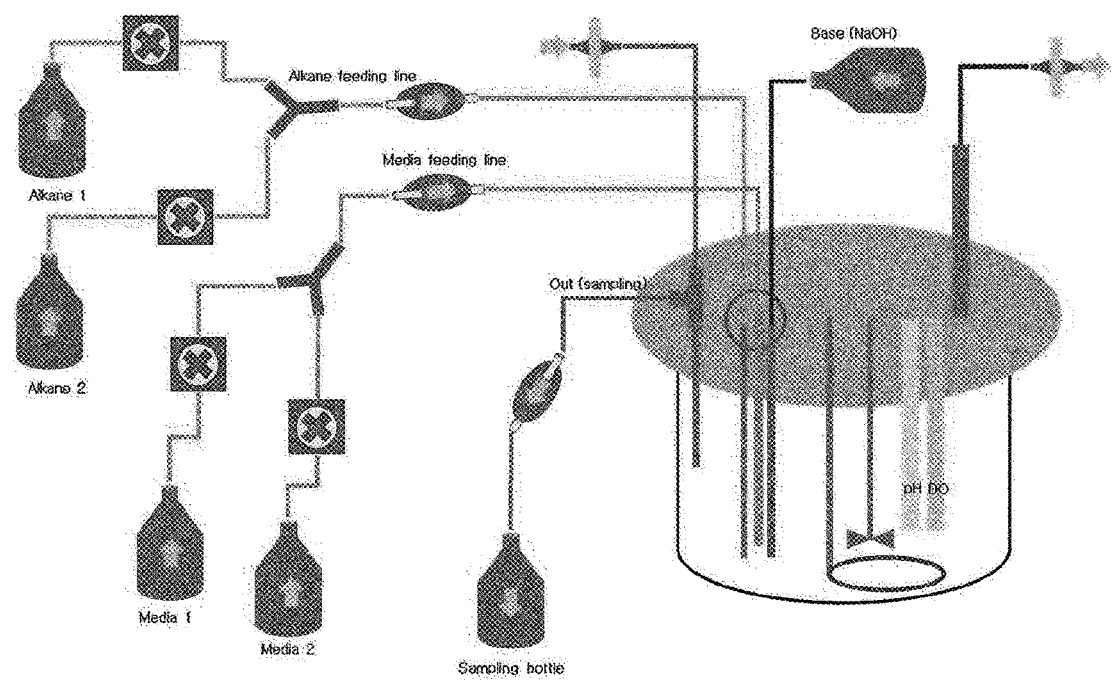
FIG. 1 is a drawing briefly representing a competition induction continuous integrated culture device.

The following microorganisms have been deposited in accordance with the terms of the Budapest Treaty with the Korean Collection for Type Cultures (KCTC), Republic of Korea, on the date indicated:

| Microorganism | Accession No. | Date |
| --- | --- | --- |
| *Candida infanticola* LC-DA01 | KCTC 13099BP | Sep. 22, 2016 |
| *Candida infanticola* DS02 Ura3⁻ | KCTC 13103BP | Sep. 22, 2016 |
| *Candida infanticola* DS02 pox1⁻ | KCTC 13104BP | Sep. 22, 2016 |
| *Candida infanticola* DS02 pox2⁻ | KCTC 13105BP | Sep. 22, 2016 |
| *Candida infanticola* DS02 pox1⁻, pox2⁻ | KCTC 13106BP | Sep. 22, 2016 |

*Candida infanticola* LC-DA01 was deposited under Accession Number KCTC 13099BP, *Candida infanticola* DS02 Ura3⁻ was deposited under Accession Number KCTC 13103BP, *Candida infanticola* DS02 pox1⁻ was deposited under Accession Number KCTC 13104BP, *Candida infanticola* DS02 pox2⁻ was deposited under Accession Number KCTC 13105BP, and *Candida infanticola* DS02 pox1⁻, pox2⁻ was deposited under Accession Number KCTC 13106BP on Sep. 22, 2019 with KCTC. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by KCTC under the terms of the Budapest Treaty, and subject to an agreement between Applicant and KCTC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. § 122 and the Commissioner's rules pursuant thereto (including 37 C.F.R. § 1.14). Availability of the deposited strain is not to be construed as a license to practice the invention in contravention of the rights granted under the authority of any government in accordance with its patent laws.

BEST MODE CARRYING OUT THE INVENTION

Various changes in form and details may be made to the presently disclosed embodiment and thus should not be construed as being limited to the aspects set forth herein. The presently disclosed embodiment is not limited to the aspects described in the present description, and thus it should be understood that the presently disclosed embodiment includes every kind of variation example or alternative equivalent included in the spirit and scope of the presently disclosed embodiment. Also, while describing the aspects, detailed descriptions about related well-known functions or configurations that may diminish the clarity of the points of the aspects of the presently disclosed embodiment will be omitted.

Hereinafter, the present invention will be described in detail.

The term 'block' used herein can be interchanged with the term 'inhibit' and may mean blocking some pathways or reactions.

Further, the term 'hydrocarbon' may refer to an organic compound consisting solely of carbon and hydrogen.

Further, 'fatty acid' may refer to a saturated or unsaturated monocarboxylic acid in the form of a chain.

Further, the term 'ω-oxidation' may mean a reaction in which the terminal methyl group of fatty acid is oxidized to dicarboxylic acid, and the term 'β-oxidation' may mean a reaction in which a β-carbon atom in a carboxyl group is oxidized to degrade while releasing acetyl CoA. In general, oxidation of fatty acid is the main reaction of β-oxidation (ω-oxidation) in which the fatty acid is cleaved from the terminal carboxyl group to two carbon units, and the ω-oxidation is understood to be a supplementary pathway for medium chain fatty acid having carbon number of 10 to 12.

According to the method for producing dioic acids of the present invention, dioic acids can be produced from a substrate containing hydrocarbons or fatty acids using *Candida infanticola* strain.

The method for producing dioic acids is characterized by comprising the following steps of: (A) culturing *Candida infanticola* strain in yeast extract glucose medium (YG medium) supplemented with a substrate containing hydrocarbons or fatty acids for securing initial cell mass;

(B) adding a carbon source or a substrate containing hydrocarbons, fatty acids or its derivatives to the culture solution of the step (A) to induce ω-oxidation reaction; and (C) culturing the reaction solution of the step (B) while adding a substrate containing hydrocarbons or fatty acids and glucose.

The culture of the step (A) may be conducted at a condition of 30±5° C., dissolved oxygen of 10% or more for 20 hr to 50 hr, and preferably it may be conducted at a condition of 30±3° C., dissolved oxygen of 30±3% for 24 hr to 48 hr. Further, the substrate may be methyl laurate, but not limited thereto.

The reaction of the step (B) may be conducted with a carbon source of 0.5% to 5% or a substrate for 10 hr to 30 hr, preferably it may be conducted with a carbon source of 0.5% to 3% or a substrate for 15 hr to 25 hr, and more preferably it may be conducted with dodecane of about 1% for 15 hr to 25 hr.

The culture of the step (C) may be conducted with the substrate of 0.1 ml/L/h to 2 ml/L/h and the glucose of 1 g/L/h to 3 g/L/h for 50 hr to 100 hr, and preferably it may be conducted with the substrate of 0.5 ml/L/h to 1 ml/L/h and the glucose of 1.5 g/L/h to 2.5 g/L/h for 80 hr to 100 hr. The substrate may be methyl laurate, but not limited thereto.

The dioic acids may be selected from the group consisting of ethanedioic acid, propanedioic acid, butanedioic acid, pentanedioic acid, hexanedioic acid, octanedioic acid, nonanedioic acid, decanedioic acid, undecanedioic acid, dodecanedioic acid, hexadecanedioic acid and a combination thereof, and preferably the dioic acids may include dodecanedioic acid.

The *Candida infanticola* strain may be selected from a wild type strain, a mutant strain, a transformant strain and a combination thereof.

Specifically, the wild type strain may be *Candida infanticola* wild type strain (*Candida infanticola* DS02; KCTC 12820BP) without genetic manipulation, the mutant strain may be *Candida infanticola* mutant strain (*Candida infanticola* LC-DA01; KCTC13099BP), and the transformant strain may be *Candida infanticola* transformant strain (*Candida infanticola*; KCTC13103BP, KCTC13104BP, KCTC13105BP, KCTC13106BP).

According to one embodiment, the *Candida infanticola* wild type strain (*Candida infanticola* DS02; KCTC 12820BP) may be a strain which uses a carbon source selected from the group consisting of hydrocarbons, fatty acids and a combination thereof.

The carbon source may be selected from hydrocarbons or fatty acids having carbon number of 6 to 30, preferably alkanes or fatty acids having carbon number of 8 to 20. For example, it may be dodecane, methyl laurate, lauric acid, its derivatives or a combination thereof, and derivatives of lauric acid may be $C_{1-8}$ alkyl laurate. Preferably, it may be selected from the group consisting of methyl laurate, ethyl laurate, propyl laurate and a combination thereof.

Further, the *Candida infanticola* mutant strain (*Candida infanticola* LC-DA01; KCTC13099BP) may be a strain which uses a substrate selected from hydrocarbons, fatty acids and a combination thereof. The mutant strain may be manufactured by a method of treating, for example, ethyl methane sulfonate (EMS), ultra violet (UV) or a combination thereof, to a wild type strain, but not limited thereto.

Further, the *Candida infanticola* transformant strain (*Candida infanticola*; KCTC13103BP, KCTC13104BP, KCTC13105BP, KCTC13106BP) may use a substrate selected from hydrocarbons, fatty acids and a combination thereof. The transformant strain can be manufactured by inducing transformation by physical stimulation such as heat-shock and electroporation, chemical stimulation such as hydroxyurea treatment, and the like, and the transformation efficiency may be enhanced, for example, by using polyethylene glycol (PEG), lithium-acetate, dimethyl sulfoxide (DMSO) and the like for heat-shock. In general, it is known that homologous recombination and non-recombinant recombination of eukaryotes such as yeast are regulated depending on the cell cycle. The homologous recombination can occur mainly in the S phase and G2 phase using chromatid for DNA replication, and for example, in order to increase probability of the homologous recombination, the cell cycle can be regulated by using hydroxyurea. Specifically, the hydroxyurea can inhibit ribonucleotide reductase and reduce the amount of dNTP to be used for DNA synthesis, thereby arresting the cell cycle in the S phase. Therefore, the probability of homologous recombination upon transformation can be increased.

According to one embodiment, the transformant strain may include a strain deleted with URA3 and POX genes. Transformation of the gene-deficient strain may be induced, for example, by applying heat-shock, hydroxyurea treatment or a combination thereof to a wild type *Candida infanticola* strain, and the order and the number of times of the application may be suitably selected by those skilled in the art. Further, according to one embodiment, the transformant strain may be a haploid. For example, in general, *Candida infanticola* strain, whose polyploidy is a haploid, may be advantageous in genetic manipulation compared with *Candida tropicalis*, which is a diploid mainly used in the production of dicarboxylic acid in industry.

Mode for Invention

Hereinafter, the present invention is explained by the following examples in more detail. The following examples are intended to further illustrate the present invention. Accordingly, those of ordinary skill in the art will recognize that various changes and modifications of the embodiments described herein can be made without departing from the scope and spirit of the invention.

Example 1: Isolation of *Candida infanticola* Wild Type Strain (*Candida infanticola* DS02; KCTC 12820BP)

A samples was collected from an oil separator (CPI, Coagulated Plate Interceptor), an aeration tank and a precipitation tank of a waste water treatment facility of petrochemical process that processes waste water through an equalization tank, an aeration tank, a precipitation tank and the like after the first treatment in the oil separator (CPI) to treat waste water from a petrochemical plant containing high concentration of various carbon sources.

The sample was prepared by collecting a waste water sample from inflow water of the oil separator, effluent water of the oil separator, effluent water of the equalization tank, inflow water of the aeration tank, effluent water of the aeration tank, inflow water of the precipitation tank and effluent water of the precipitation tank in a 1 L sterilized water sample pack, and the collected sample was placed in an ice box and transferred to a laboratory. A portion of the collected sample was first spread on a solid medium (agar plate) made of the primary culture medium composition shown in the following Table 1, and cultured in a 30° C. constant temperature incubator for 1 week. After the culture, in order to select strains with high growth rate in a culture solution containing dodecane ($C_{12}$ alkane), colonies generated on the solid medium were collected, inoculated into competition induction continuous integrated culture medium containing dodecane ($C_{12}$ alkane) as the only carbon source, made of the subculture medium composition shown in the following Table 1, and then cultured in the competition induction continuous integrated culture device (FIG. 1) at a condition of 30° C., quantity of airflow of 1 v/v/m, agitation speed of 400 rpm and pH 5.0 (controlled by 10N NaOH).

Figure 2:
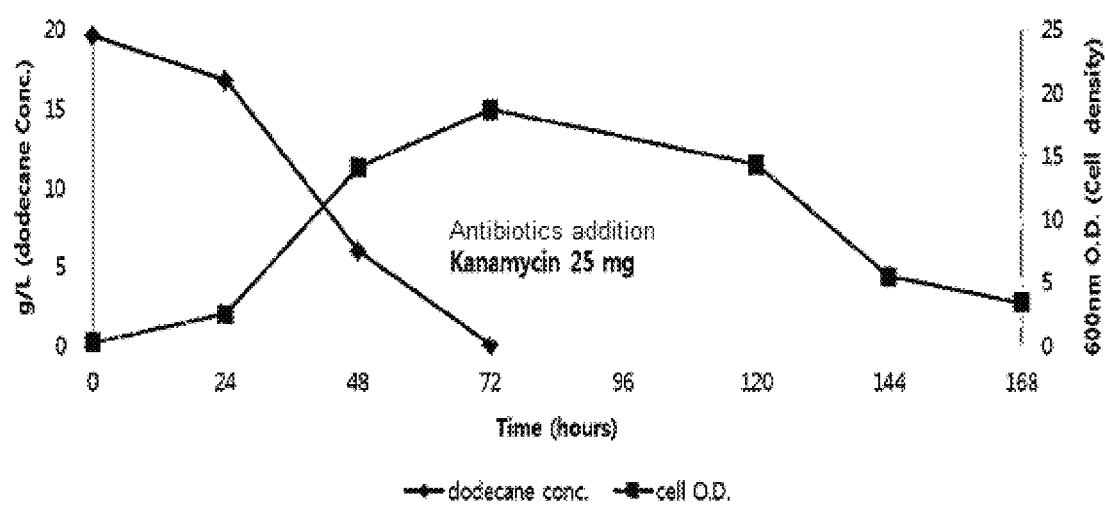
FIG. 2 is a graph showing change on OD value of microorganism in competition induction continuous integrated culture over time.
Figure 3:
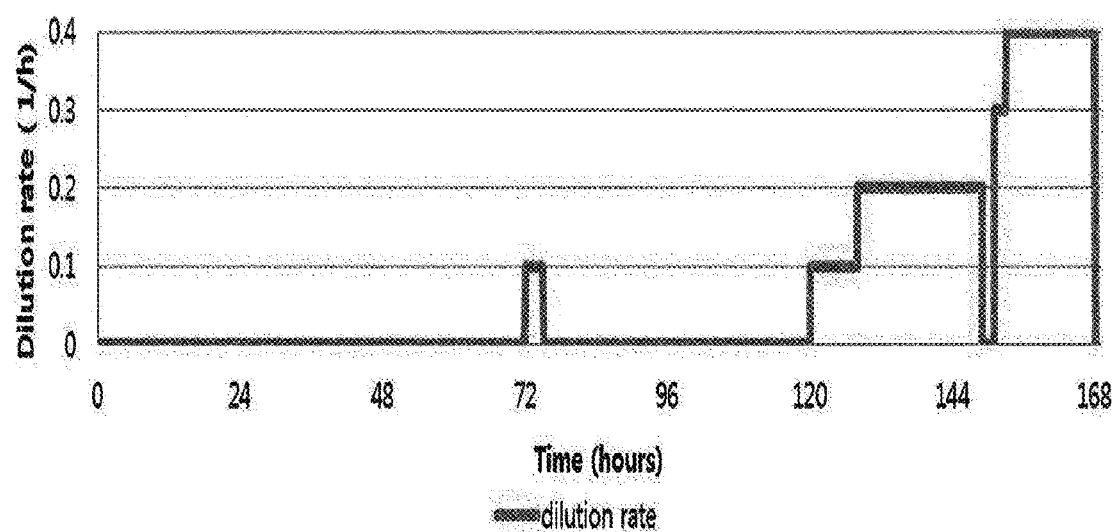
FIG. 3 is a graph showing change on dilution rate of microorganism in competition induction continuous integrated culture over time.

After consumed the initially added dodecane of 20 g/L during the competition induction continuous integrated culture, the additional medium of the following Table 2 containing dodecane of 40 g/L additionally was added thereto and then dilution rate was increased from 0 to 0.4, thereby finally isolating *Candida infanticola* wild type strain (*Candida infanticola* DS02; KCTC 12820BP) as a strain having the best growth. In this experiment, antibiotics kanamycin of 25 mg/L was used to inhibit the growth of some microorganisms. The results of the above experiments were shown in FIG. 2 and FIG. 3.

TABLE 1

| Medium composition | Primary culture medium (Solid medium) | Competition induction continuous integrated culture medium | |
|---|---|---|---|
| | | Subculture medium | Additional medium |
| YNB (Yeast nitrogen base without amino acid) | 6.7 g/L | 20 g/L | 20 g/L |
| Dodecane | 10 g/L | 20 g/L | 40 g/L |
| Surfactant | Gum Arabic 0.5% | Tween 80 3 mL/L | Tween 80 3 mL/L |

Test Example 1: 18s rRNA Genetic Analysis of Isolated Strain

The isolated strain isolated in Example 1 was analyzed by 18s rRNA base sequence analysis. Genomic DNA of the isolated strain of Example 1 was extracted by using a Yeast gDNA prep kit (PureHelix™, NANOHELIX), and then the extracted genomic DNA as a template was amplified by PCR using the 18s ITS ¼ primer shown in the following Table 2. After cloning TA vector, 18s rRNA base sequence was obtained through DNA sequencing reaction, and the base sequence was shown in FIG. 4 as SEQ ID NO. 1.

TABLE 2

| | Base sequence (5' → 3') | SEQ ID NO. |
|---|---|---|
| Forward primer | TCC GTA GGT GAA CCT GCG G | SEQ ID NO. 2 |
| Reverse primer | TCC TCC GCT TAT TGA TAT GC | SEQ ID NO. 3 |

For the base sequence of the isolated strain shown in FIG. 4 (SEQ ID NO. 1), homology of the strain was examined using BLAST (Basic Local Alignment search tool) of NCBI (National Center for Biotechnology Information). The results of the examination were shown in the following Table 3.

As shown in the following Table 3, it can be confirmed that the isolated strain is allied species having high homology with *Candida infanticola* CBS11940.

TABLE 3

| Isolated strain | SEQ ID NO: and Sequence length | Allied species | Homology |
|---|---|---|---|
| *Candida infanticola* DS02 | SEQ ID NO. 1 434 bp | *Candida infanticola* strain CBS11940 (HQ695010) | 99% |

Test Example 2: Carbon Source Assimilation Ability Analysis of *Candida infanticola* Wild Type Strain (*Candida infanticola* DS02; KCTC 12820BP)

In order to check carbon source assimilation ability of the above strain (*Candida infanticola* wild type strain (*Candida infanticola* DS02; KCTC 12820BP)), API 20c AUX (Biomerieux company) was used for analysis. The results of the experiments analyzed by using API 20c AUX (Biomerieux company) was compared with the existing *Candida infanticola* kurtzman and *Candida infanticola* sp., and the results were shown in the following Table 4.

TABLE 4

| Carbon source | Example 1 (*Candida infanticola* DS02; KCTC 12820BP) | Comparative Example 1 (*Candida infanticola* kurtzman) | Comparative Example 2 (*Candida infanticola* sp.) |
|---|---|---|---|
| Glucose | + | + | + |
| Glycerol | − | + | + |
| 2-Keto-D-gluconate | − | − | − |
| L-Arabinose | − | − | − |
| D-Xylose | − | − | − |
| Adonitol | − | − | − |
| Xylitol | − | − | − |
| D-galactose | − | + | + |
| Inositol | − | − | − |
| D-Sorbitol | − | + | + |
| A-Methyl-D-glucoside | − | − | − |
| N-Acetyl-D-glucosamine | − | − | − |
| D-Cellobiose | − | − | − |
| D-Lactose | − | − | − |
| D-Maltose | − | − | − |
| D-Saccharose (Sucrose) | − | − | − |
| D-Trehalose | − | − | − |
| D-Melezitose | − | − | − |
| D-Raffinose | − | − | − |

As shown in the above Table 4, when comparing Comparative Example 1 (*Candida infanticola* kurtzman) and Comparative Example 2 (*Candida infanticola* sp.) with *Candida infanticola* wild type strain (KCTC 12820BP) (Example 1), it can be confirmed that the previously known *Candida infanticola* strains of Comparative Example 1 and Comparative Example 2 have assimilation ability for the carbon source, i.e., glucose, glycerol, D-galactose and D-sorbitol, whereas the *Candida infanticola* wild type strain (KCTC 12820BP) can use only glucose as a carbon source. As shown in the above experiment results, it can be found that the novel *Candida infanticola* wild type strain (KCTC 12820BP) of the present invention shows a large difference in carbon assimilation ability compared with the existing strains.

Test Example 3: Optimum Growth pH of *Candida infanticola* Wild Type Strain (*Candida infanticola* DS02; KCTC 12820BP)

In order to check the optimum growth pH of *Candida infanticola* wild type strain (*Candida infanticola* DS02; KCTC 12820BP), initial pH of yeast nitrogen base (YNB) medium without amino acid was variously set from 4 to 7, and the strain was cultured in the medium. The results of the experiment were shown in FIG. 5.

Figure 5:
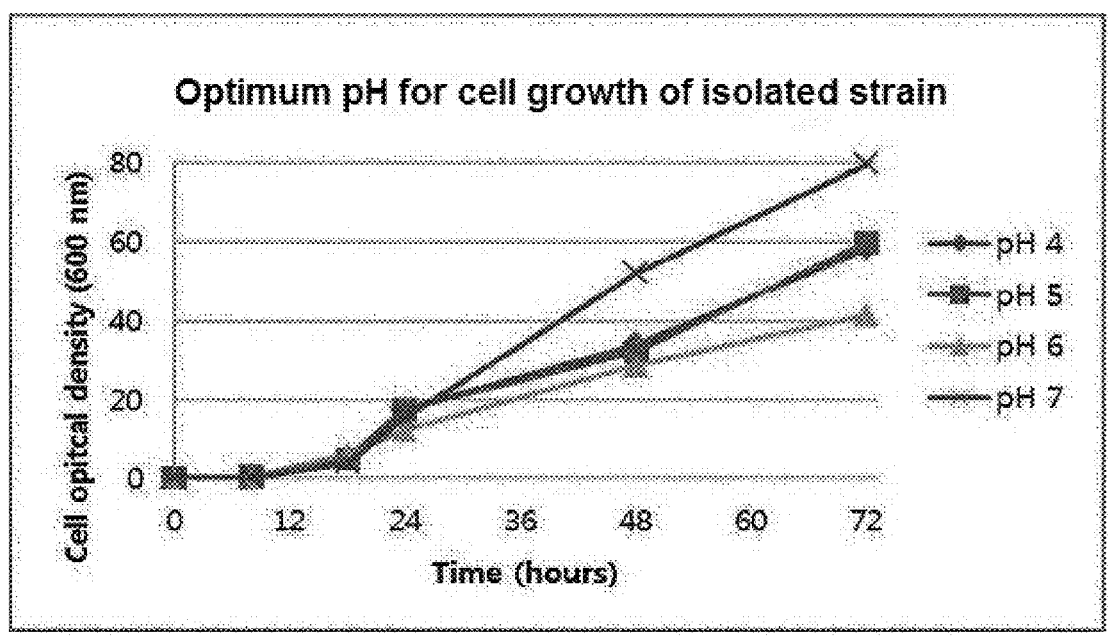
FIG. 5 is a graph showing growth rate of an isolated strain (*Candida infanticola* wild type strain (*Candida infanticola* DS02; KCTC 12820BP)) by pH.

As shown in FIG. 5, it can be confirmed that the optimum growth pH of *Candida infanticola* wild type strain (KCTK 12820BP) is pH 7.

Test Example 4: Comparison of Alkane ($C_{12}$) Substrate Uptake Rate when Culturing *Candida infanticola* Wild Type Strain (*Candida infanticola* DS02; KCTC 12820BP) with Alkane ($C_{12}$) as Only Carbon Source In order to check alkane ($C_{12}$) consumption rate and amount of the produced cell in alkane ($C_{12}$) substrate culture of *Candida infanticola* wild type strain (*Candida infanficola* DS02; KCTC 12820BP), as shown in the following Table 5, the *Candida infanficola* wild type strain (*Candida infanticola* DS02; KCTC 12820BP) of Example 1 and *Candida tropicalis* (ATCC 20336) as a comparison standard strain were cultured in yeast extract medium containing dodecane of 20 g/L as the only carbon source. The results of the experiment were shown in FIG. 6.

TABLE 5

| | Composition | | Amount (g/L) |
|---|---|---|---|
| | Dodecane | | 20 |
| | $MgSO_4 \cdot 7H_2O$ | | 1 |
| | Yeast extract | | 20 |
| | $(NH_4)_2SO_4$ | | 8 |
| | $KH_2PO_4$ (monobasic) | | 2 |
| | NaCl | | 0.1 |
| | $CaCl_2 \cdot 2H_2O$ | | 0.1 |
| Trace element solution | $CaCl_2 \cdot 2H_2O$ | 13.2 g/L | 1 ml |
| | $FeSO_4 \cdot 7H_2O$ | 8.4 g/L | |
| | $MnSO_4 \cdot 4H_2O$ | 2.4 g/L | |
| | $ZnSO_4 \cdot 7H_2O$ | 2.4 g/L | |
| | $CuSO_4 \cdot 5H_2O$ | 0.48 g/L | |
| | $CoCl_2 \cdot 6H_2O$ | 0.48 g/L | |
| | $Na_2MoO_4 \cdot 2H_2O$ | 0.24 g/L | |
| | $K_2B_4O_7 \cdot 4H_2O$ | 0.06 g/L | |
| | $CaCl_2 \cdot 2H_2O$ | 13.2 g/L | |
| | Antifoam | | 0.5 ml |

Figure 6:
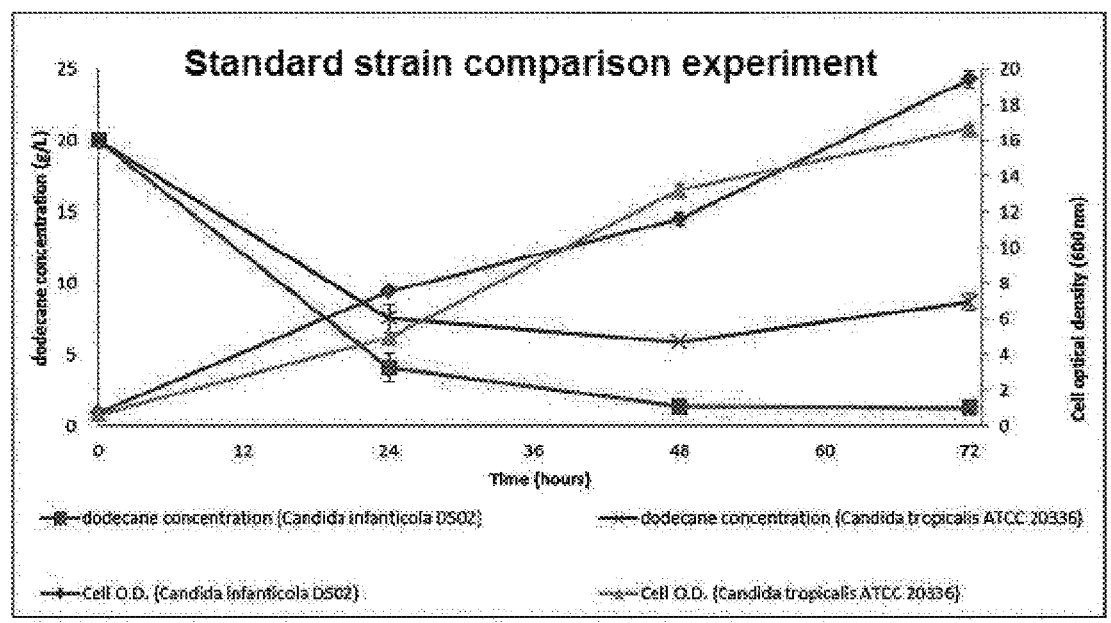
FIG. 6 is a graph showing dodecane consumption rate and amount of the produced cell for *Candida infanticola* wild type strain (KCTC 12820BP) and *Candida tropicalis* (ATCC 20336) over time.

As shown in FIG. 6, it can be confirmed that the dodecane consumption rate of the *Candida infanticola* DS02 was 6.2 g/L per day that was 1.6 times faster than the dodecane consumption rate of the *Candida tropicalis*, used as a comparison strain, of 3.7 g/L per day. In addition, it can be confirmed that the amount of the produced cell was also 17% higher.

Example 2: Conversion of Dodecane into DDDA (Dodecanedioic Acid) by *Candida infanticola* Wild Type Strain (*Candida infanticola* DS02; KCTC 12820BP)

Figure 7:
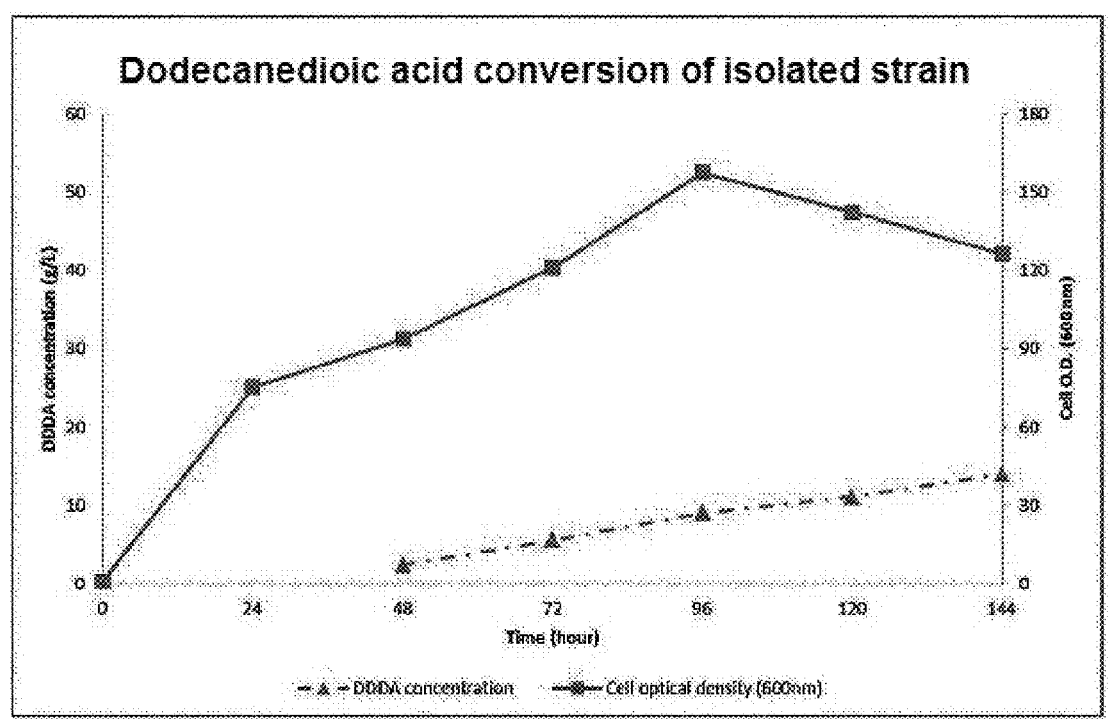
FIG. 7 is a graph showing dodecanedioic acid (DDDA) conversion of dodecane by *Candida infanticola* wild type strain (*Candida infanticola* DS02; KCTC 12820BP).
Figure 8:
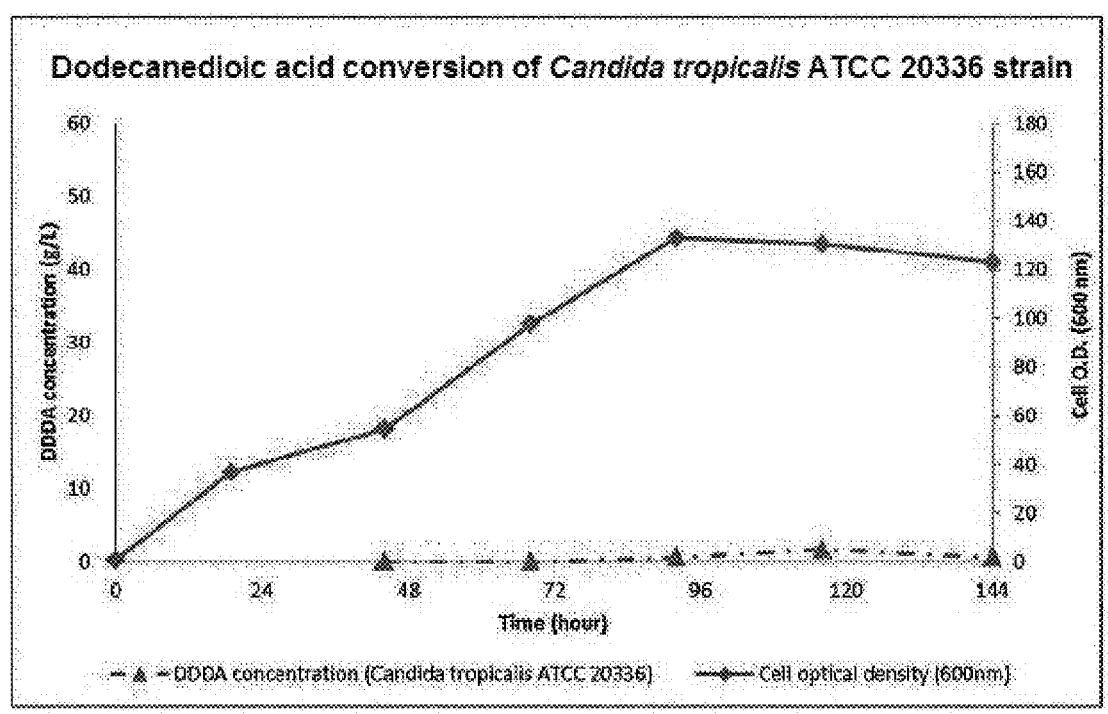
FIG. 8 is a graph showing dodecanedioic acid (DDDA) conversion of dodecane by *Candida tropicalis* (ATCC20336).

In order to obtain the initial cell mass for conversion of dodecane into DDDA (dodecanedioic acid) by *Candida infanticola* wild type strain (*Candida infanticola* DS02; KCTC 12820BP), wild type strain *Candida tropicalis* (ATCC 20336) that belongs to the same species with the strain and not genetically manipulated, *Candida parapsilosis* and *Pichia caribbica*, the *Candida infanticola* wild type strain (*Candida infanticola* DS02; KCTC 12820BP) of Example 1 was cultured in yeast extract medium that contains glucose of 50 g/L and uses methyl laurate substrate for 24 hr to 48 hr at a condition of 30° C., quantity of airflow of 1 v/v/m, agitation speed of dissolved oxygen (DO) of 30% (100 rpm to 900 rpm depending on DO value) and pH 5, and then ω-oxidation was induced using 1% dodecane at pH 7 for 12 hr to 20 hr. Then, the cultured was continued for 9 hr while adding methyl laurate of 0.5 ml/L/h to 1.0 ml/L/h and glucose of 2 g/L/h to conduct the DDDA conversion at pH 7 to pH 8. The results of the experiment were shown in FIG. 7, FIG. 8 and the following Table 6.

TABLE 6

| Result of 144 hr culture | O.D. (max.) | DDDA concentration (g/L) |
|---|---|---|
| Example 1 (*Candida infanticola* DS02; KCTC 12820BP) | 157.4 | 14.0 |
| Comparative Example 3 (*Candida tropicalis*; ATCC 20336) | 133.1 | 0.62 |
| Comparative Example 4 (*Candida parapsilosis*) | 146.8 | 0 |
| Comparative Example 5 (*Pichia caribbica*) | 141.8 | 0 |

As shown in the above Table 6, as the result of the culture for 144 hr, it can be confirmed that Example 1 (*Candida infanticola* DS02; KCTC 12820BP) showed O.D (optical density) value of 157 and DDDA concentration of 14.0 g/L that was much higher than O.D value of 133.1 and DDDA concentration of 0.62 g/L of Comparative Example 3 (*Candida tropicalis*; ATCC 20336), and there was no DDDA conversion and the added carbon source was only used for cell growth in Comparative Example 4 and Comparative Example 5.

Example 3: Induction and Screening of Mutant for Wild Type *Candida infanticola* Strain The wild type *Candida infanticola* (*Candida infanticola* DS02; KCTC 12820BP) strain can grow by using dodecane as single carbon source, but a mutant strain in which β-oxidation pathway is blocked cannot substantially grow by using dodecane as single carbon source. The "cannot substantially grow" means "dose not grow" or "grow a little". Thus, a mutant strain was selected by comparing strain growth in solid medium containing glucose or dodecane as single carbon source.

In order to induce mutation to the selected mutant strain, ethyl methane sulfonate (EMS) and UV were used. Using phosphate buffered saline (PBS) buffer, the *Candida infanticola* (*Candida infanticola* DS02; KCTC 12820BP) strain suspension having OD (optical density 600 nm) of 0.01 to 0.1 was prepared, and 2% EMS (ethyl methane sulfonate) mutagen was added thereto to adjust to 1 ml. The suspension was reacted at 30° C., 150 rpm for 120 min, centrifuged to remove supernatant, and then washed with 20% sodium thiosulfate two times to remove the EMS. Then, the strain was suspended in 1 ml PBS buffer. 10 µl of the suspension was spread on YPD solid medium and cultured at 30° C. for 3 days to obtain a primary mutant strain survived within 10%.

The strain treated with EMS mutagen was suspended in PBS (phosphate buffered saline) to OD of 0.01 to 0.1. 10 μl of the suspension was spread on YPD solid medium, irradiated with UV (ultraviolet 254 nm) for 120 sec, and cultured at 30° C. for 3 days to obtain a secondary mutant strain survived within about 10%. The mutagenesis process can be performed by UV irradiation after EMS treatment, EMS treatment after UV irradiation, or EMS or UV alone, and the order and the number of times of mutation can be appropriately selected by those skilled in the art.

Figure 9:
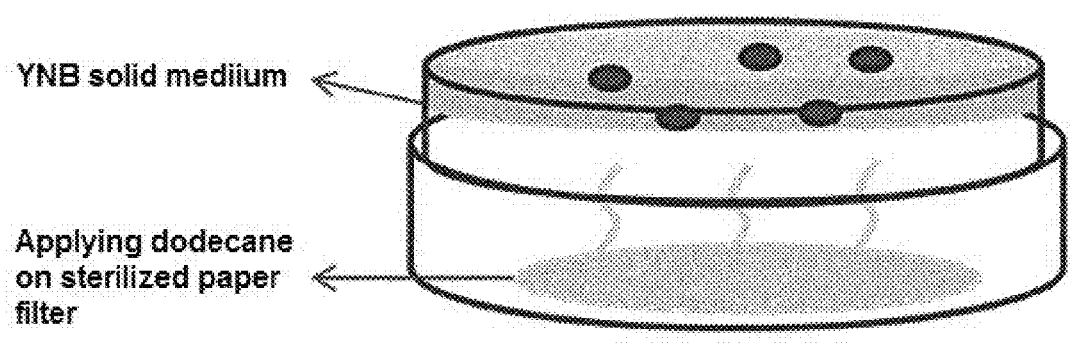
FIG. 9 is a schematic diagram about manufacture of solid medium using steam.

In order to select a mutant strain in which β-oxidation is blocked by mutagenesis, strain growth on solid medium containing glucose or dodecane as single carbon source was compared. The composition of the used solid medium was as follows: solid medium (YNB, yeast nitrogen base without amino acid) using glucose as single carbon source 6.7 g/L and glucose 10 g/L, and solid medium (YNB, yeast nitrogen base without amino acid) using dodecane as single carbon source 6.7 g/L and dodecane 10 g/L. In the case of the solid medium containing dodecane whose color is opaque white, it is not easy to identify grown colony. Therefore, solid medium was prepared by using dodecane vapor and strain growth was efficiently compared. The solid medium was illustrated in FIG. 9.

The procedure was performed as follows: a filter of sterilized paper is put into solid medium, a fixed amount of dodecane is applied on the filter, dodecane is spread in the solid medium as a vapor during solid culture, and the strain uses the dodecane. Candidate mutant strain was suspended in PBS buffer to obtain strain suspension having OD of 0.01 to 0.1, 10 μl of the suspension was inoculated on the two solid medium described above using a micropipette and then cultured at 30° C. for 3 days. The primary selection was conducted by selecting a strain that grows well on the glucose solid medium but does not grow on the dodecane solid medium because β-oxidation was blocked.

The primarily selected mutant strain was grown in liquid medium containing dodecane as single carbon source to secondarily select a β-oxidation gene-blocked strain. In this Example, total 6 selected strains were subjected to liquid culture. The liquid culture was conducted as follows: each selected strain was inoculated in a culture solution containing 70 ml dodecane as single carbon source in a 250 ml flask (Erlenmeyer flask) to first culture OD of 1 and cultured at 30° C., 150 rpm for 6 days. The composition of the used liquid medium was medium (YNB, yeast nitrogen base without amino acid) using dodecane as single carbon source 20 g/L and dodecane 20 g/L. Each culture result was shown in graphs of FIG. 10, which shows OD values measured for mutant strains that did not use dodecane as a carbon source and mutant strains that used dodecane. The strains not used dodecane was determined as the strains in which β-oxidation was blocked to complete the secondary selection. The β-oxidation-blocked mutant strain was named as *Candida infanticola* LC-DA01, and deposited to Korean Collection for Type Cultures of Korea Research Institute of Bioscience and Biotechnology (Accession No.: KCTC13099BP, Sep. 8, 2016).

Figure 10:
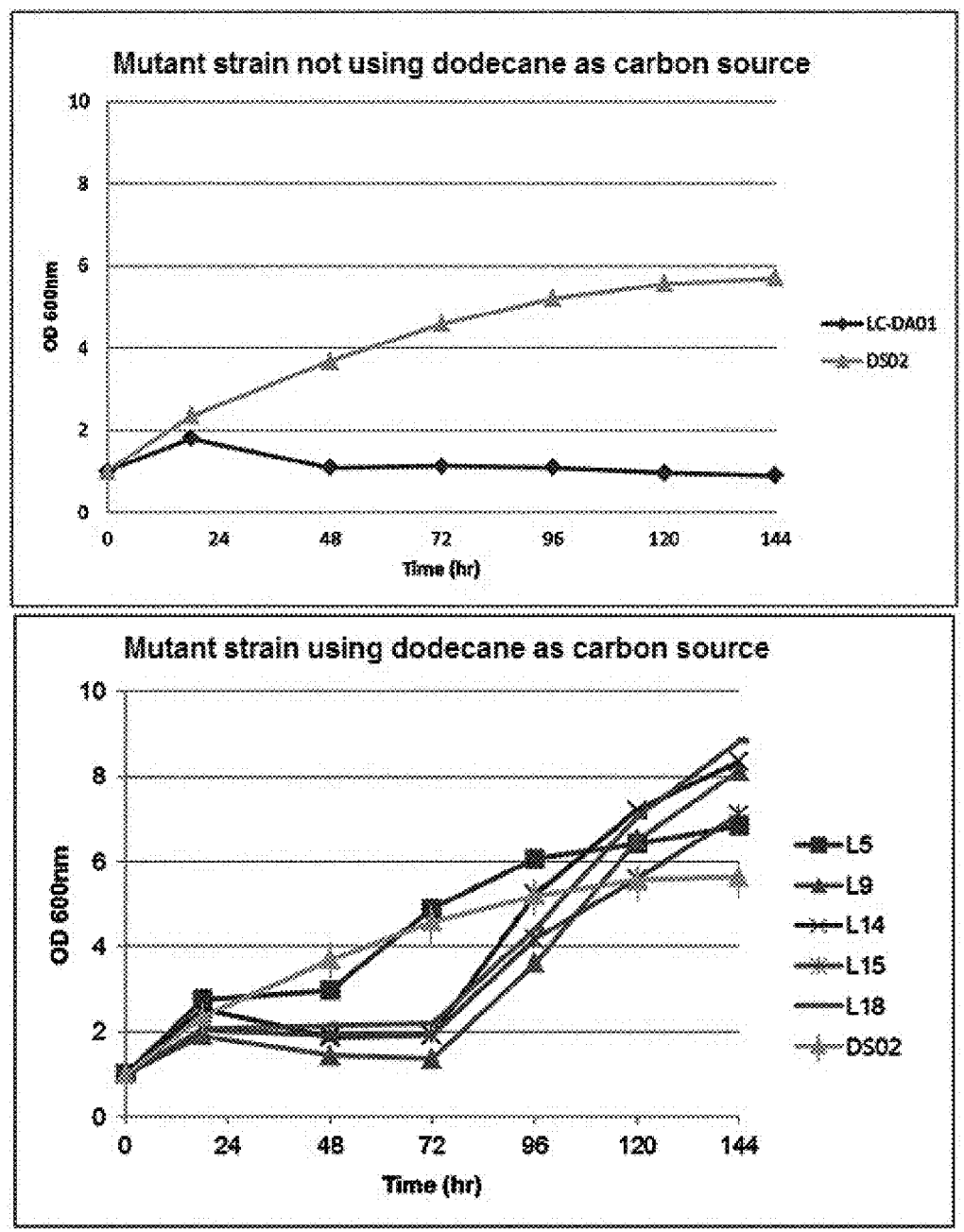
FIG. 10 is a graph showing OD value according to the presence or absence of single carbon source for *Candida infanticola* mutant strain (*Candida infanticola* LC-DA01: KCTC13099BP).

As shown in FIG. 10, it can be primarily confirmed that β-oxidation pathway of the mutant strain (Accession No.: KCTC13099BP) was blocked.

Example 4: Dioic Acids Conversion Culture of *Candida infanticola* Mutant Strain Using Fatty Acid Substrate In order to obtain the initial cell mass for dodecanedioic acids (DDDA) conversion of methyl laurate by *Candida infanticola* mutant strain (Accession No.: KCTC13099BP), *Candida infanticola* mutant strain (*Candida infanticola* LC-DA01; Accession No.: KCTC13099BP) was cultured in yeast extract medium, which contains glucose 50 g/L and supplemented with methyl laurate substrate, at 30° C., agitation speed of dissolved oxygen (DO) of 30% (100 rpm to 900 rpm depending on DO value) and pH 5 for 24 hr to 48 hr. At 12 hr to 24 hr during the culture, after completely consuming glucose of 50 g/L, glucose was added at 1 g/L/h to 4 g/L/h until the culture was finished.

Figure 11:
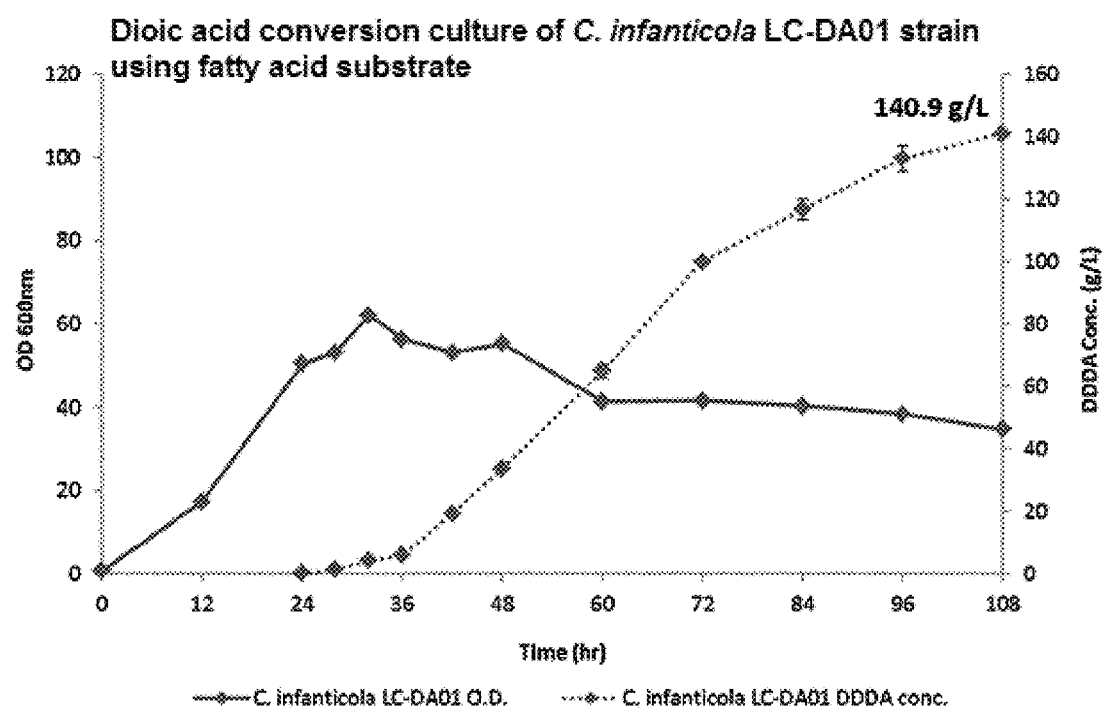
FIG. 11 is a graph showing the result of converting dioic acids of a mutant strain by using fatty acids.

After obtaining the initial cell mass, ω-oxidation was induced using 1% dodecane at pH 7 for 12 hr to 20 hr, and culture was continued for 96 hr to 144 hr while adding methyl laurate at 0.5 ml/L/h to 4.0 ml/L/h and glucose at 1 g/L/h to 4 g/L/h to conduct DDDA conversion at pH 7 to pH 8. The results were shown in FIG. 11 and Table 7.

TABLE 7

| C. infanticola | Wild type DS02; KCTC 12820BP | Mutant (β-oxidation-blocked Lotte LC-DA01) |
|---|---|---|
| Cell amount (O.D.) (Maximum/Final) | 184.0/159.8 | 62.1/36.2 |
| DDDA concentration (g/L) | 10.6 | 140.9 |
| DDDA productivity (g/L/h) | 0.07 | 1.67 |
| DDDA conversion yield (DDDA/substrate) | 0.08 | 0.90 |

It can be confirmed that, after 108 hr culture, the β-oxidation-blocked *Candida infanticola* mutant strain (*Candida infanticola* LC-DA01; Accession No.: KCTC13099BP) showed O.D (optical density, maximum/final) value of 62.1/36.2, DDDA concentration of 140.9 g/L (conversion yield of 90%) and DDDA productivity of 1.67 g/L/h, and the DDDA concentration was 13 times or more higher than DDDA concentration of 10.6 g/L of the wild type *Candida infanticola* strain (*Candida infanticola* DS02; KCTC 12820BP) in which β-oxidation was not blocked.

Example 5: Dioic Acids Conversion Culture of *Candida infanticola* Mutant Strain Using Hydrocarbon Substrate In order to obtain the initial cell mass for dioic acids conversion of dodecane and decane by *Candida infanticola* mutant strain (KCTC13099BP), *Candida infanticola* mutant strain (*Candida infanticola* LC-DA01; Accession No.: KCTC13099BP) was cultured in yeast extract medium, which contains glucose 50 g/L and supplemented with methyl laurate substrate, at 30° C., agitation speed of dissolved oxygen (DO) of 30% (100 rpm to 900 rpm depending on DO value) and pH 5 for 24 hr to 48 hr. At 12 hr to 24 hr during the culture, after completely consuming glucose of 50 g/L, glucose was added at 1 g/L/h to 4 g/L/h until the culture was finished.

Figure 12:
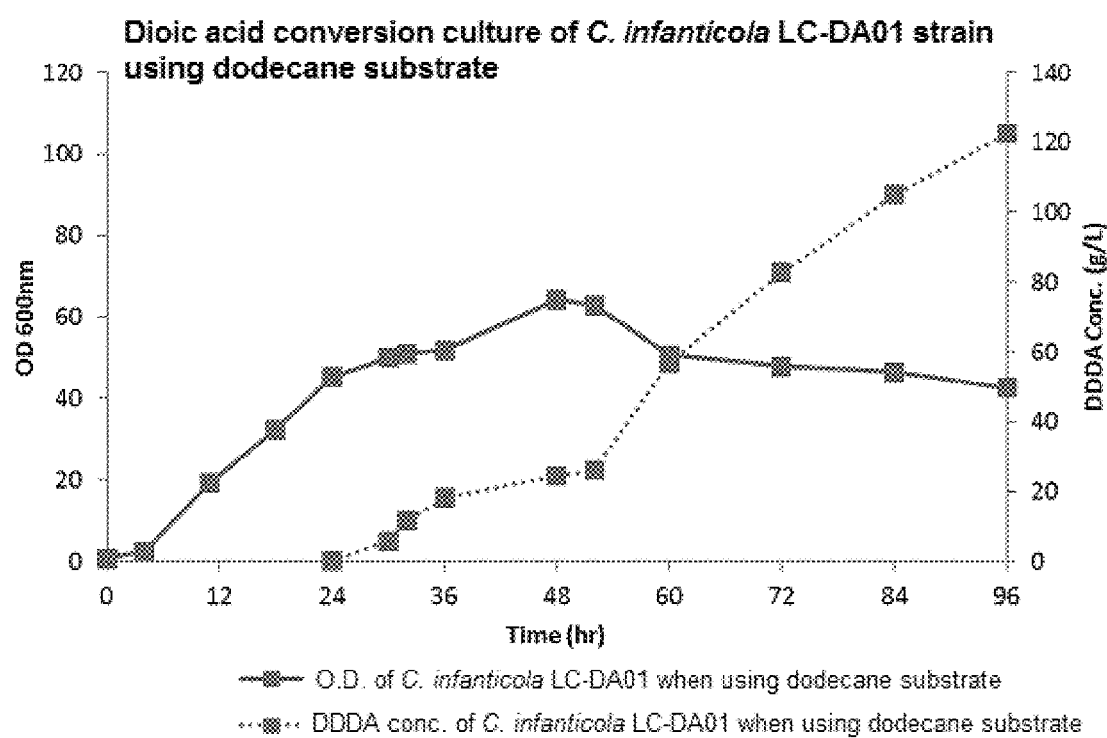
FIG. 12 is a graph showing the result of converting dioic acids of a mutant strain by using dodecane.
Figure 13:
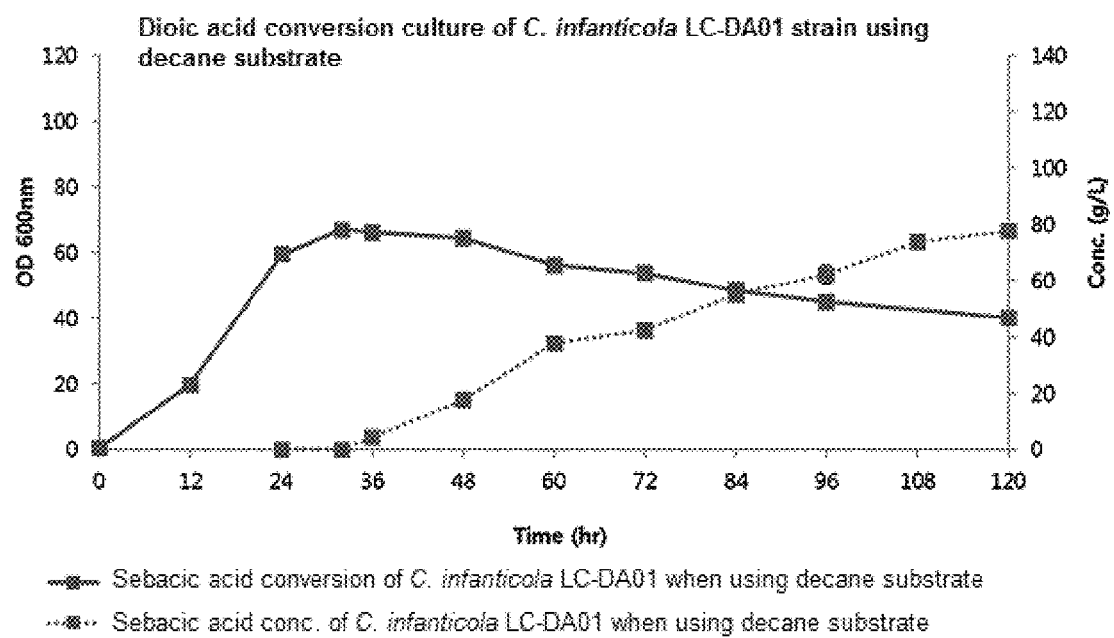
FIG. 13 is a graph showing the result of converting dioic acids of a mutant strain by using decane.

After obtaining the initial cell mass, ω-oxidation was induced using 1% dodecane at pH 7 for 12 hr to 20 hr, and culture was continued for 96 hr to 144 hr while adding dodecane and decane substrate at 0.5 ml/L/h to 4.0 ml/L/h and glucose at 1 g/L/h to 4 g/L/h to conduct DDDA conversion at pH 7 to pH 8. The results for dodecane substrate were shown in FIG. 12 and the results for decane substrate were shown in FIG. 13 and Table 8.

TABLE 8

| C. infanticola LC-DA01 | DDDA production using dodecane substrate | Sebacic acid production using decane substrate |
|---|---|---|
| Cell amount (O.D.) (maximum/final) | 64.2/42.6 | 66.9/40.0 |
| DDDA/sebacic acid concentration (g/L) | 122.5 | 77.6 |
| DDDA/sebacic acid productivity (g/L/h) | 1.70 | 0.81 |
| DDDA conversion yield (DDDA/substrate) | 0.99 | 0.75 |

It can be confirmed that, after 96 hr culture, the dodecane substrate fermentation results of the β-oxidation-blocked *Candida infanticola* mutant strain (*Candida infanticola* LC-DA01; Accession No.: KCTC13099BP) showed O.D (optical density, maximum/final) value of 64.2/42.6, DDDA concentration of 122.5 g g/L (conversion yield of 99%) and DDDA productivity of 1.70 g/L/h, and therefore, dioic acids productivity can be enhanced by using hydrocarbons as a substrate due to blocked β-oxidation.

Further, it can be confirmed that, after 96 hr culture, the decane substrate fermentation results of the β-oxidation-blocked *Candida infanticola* mutant strain (*Candida infanticola* LC-DA01; Accession No.: KCTC13099BP) showed O.D (optical density, maximum/final) value of 66.9/40.0, sebacic acid concentration of 77.6 g/L (conversion yield of 99%) and sebacic acid productivity of 0.75 g/L/h, and therefore, dioic acids productivity can be enhanced by using hydrocarbons as a substrate due to blocked β-oxidation.

Test Example 5: Optimization of Transformation Method

Figure 14:
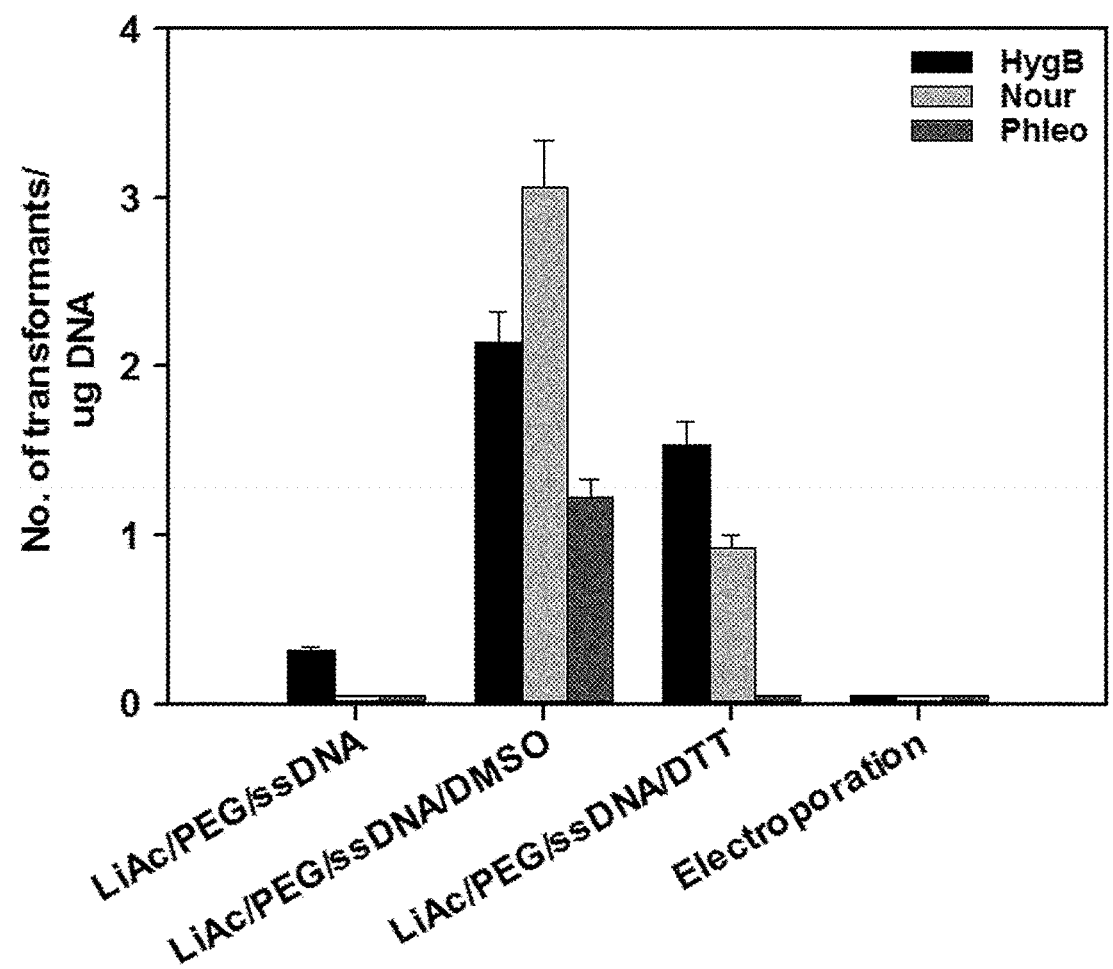
FIG. 14 is a graph showing the result of transformation of a strain by heat-shock.

In order to obtain a transformant strain, as a transformation method for introducing a foreign gene, heat-shock method using polyethylene glycol (PEG) and lithium-acetate, which are mainly used in yeast, was use. A strain was cultured on YPED solid medium at 30° C. for 20 hr to 24 hr. 2×10$^6$ cells of *Candida infanticola* (*Candida infanticola* DS02; KCTC 12820BP) were collected and suspended in a buffer containing a mixture of 50% polyethylene glycol and lithium-acetate. The suspension was reacted at 30° C. for 45 min and at 42° C. for 15 min and then the supernatant was removed. The cells were resuspended in YPED medium, cultured with shaking at 30° C. for 6 hr, spread on YEPD medium containing antibiotics and cultured at 30° C. for 3 days. In order to increase transformation efficiency, the most efficient methods were compared by adding chemicals such as dithiothreitol (DTT) and dimethyl sulfoxide (DMSO) during the heat-shock process. As a result, it was confirmed that the heat-shock method treated with DMSO was the most efficient, and the results were shown in FIG. 14.

Test Example 6: Cell Cycle Regulation Using Hydroxyurea

Figure 15:
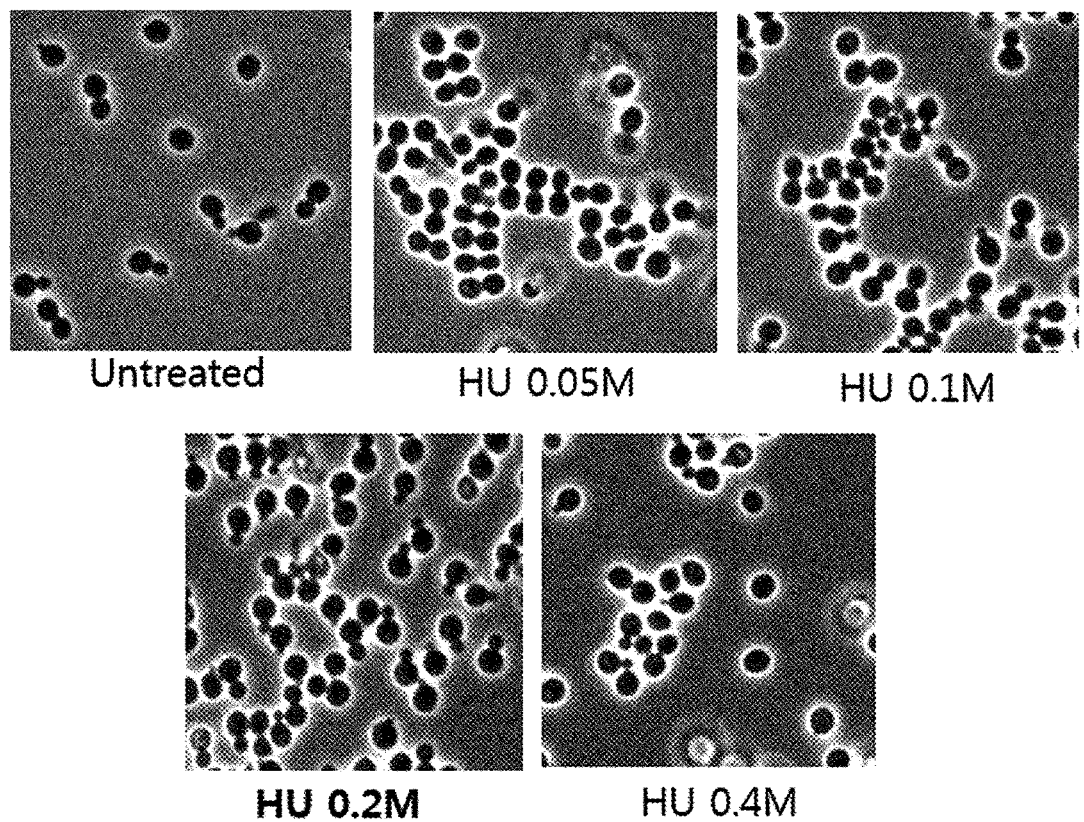
FIG. 15 is a phase difference microscopic image showing the condition of cells according to the hydroxyurea concentration.

The homologous recombination can occur mainly in the S phase and G2 phase using chromatid for DNA replication. Therefore, in order to increase probability of the homologous recombination, cell cycle was regulated using hydroxyurea. 10$^7$ cells/20 ml of *Candida infanticola* (*Candida infanticola* DS02; KCTC 12820BP) growing in YEPD medium was treated with 0.2 M hydroxyurea and reacted for 2 hr. As a result, it was confirmed that S phase cells were observed most frequently. The results were shown in FIG. 15.

Example 6: Obtaining of Uracil Auxotroph Strain

As a result of transformation of the cells of *Candida infanticola* (*Candida infanticola* DS02; KCTC 12820BP) cell cycle-arrested in the S phase by heat-shock and hydroxyurea treatment mentioned above, a uracil auxotroph strain (Accession No.: KCTC13103BP), in which a foreign gene was replaced at the position of URA3 gene, was obtained.

Figure 16:
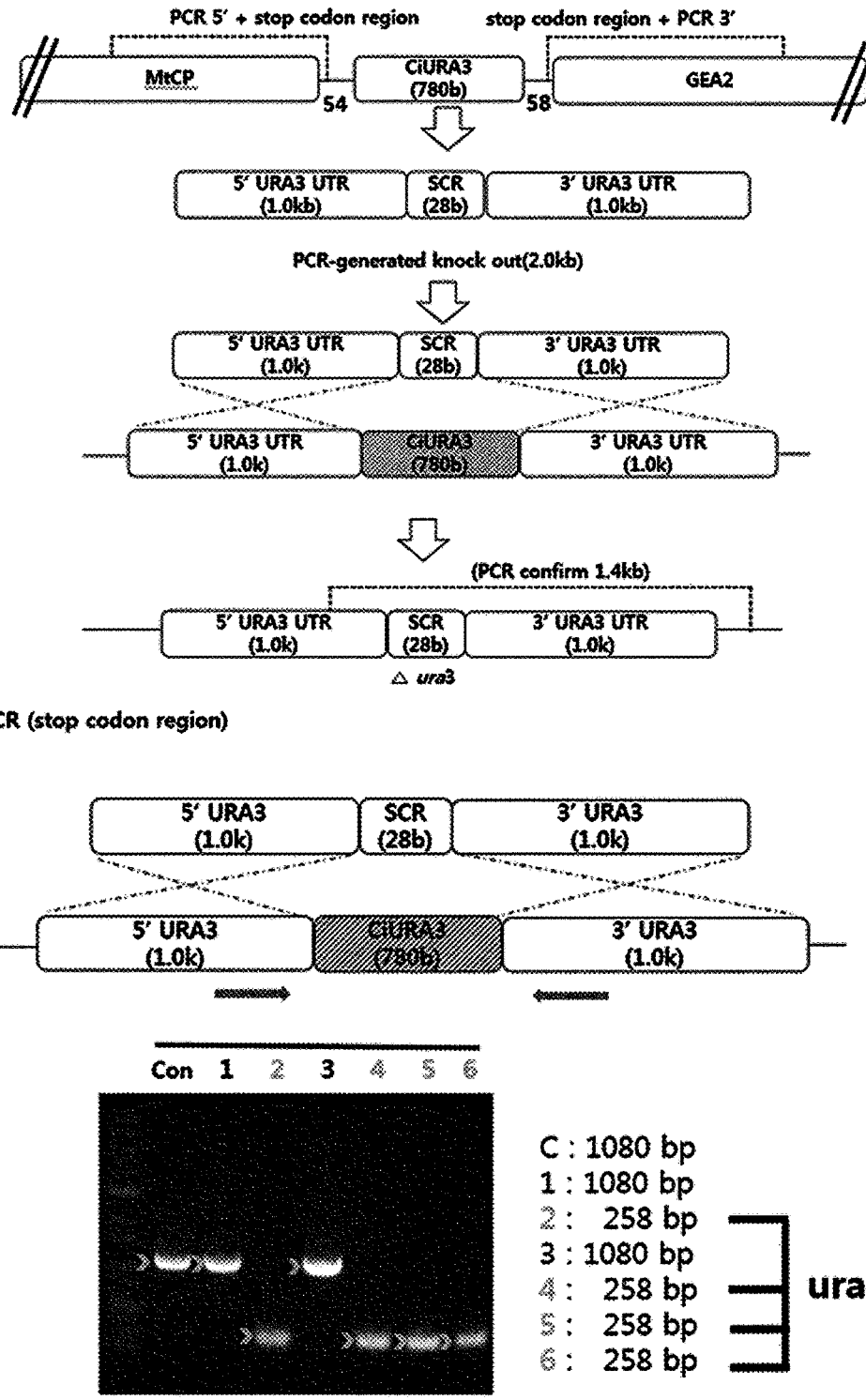
FIG. 16 is a mimetic diagram of a cassette for manufacturing a uracil auxotroph strain and the result of gDNA PCR.

As selection medium, minimal medium supplemented with uracil and 5-fluororotic acid (5'-FOA) was used, and a mimetic diagram for manufacturing the uracil auxotroph strain and the result of confirming sequence using gDNA FOR were shown in FIG. 16.

The 5-fluoorotic acid (5'-FOA) is converted to 5-fluorouracil, a harmful substance, during the synthesis of uracil, thereby leading to apoptosis. Therefore, the URA3 gene-deficient strain can grow on medium containing uracil and 5'-FOA but cannot grow on medium without uracil.

Example 7: Selection of β-Oxidation Gene

In order to remove acyl-CoA oxidase (pox gene), an enzyme that converts fatty acyl-CoA to 2 trans-enoyl-CoA in the first step of β-oxidation, amino acid sequences of POX4, POX5 and POX2 genes of *Candida tropicalis* 20336 were compared. As a result, homology of two genes, CINF_04670 and CINF_13455 were the highest as 40% or more, and the genes were named as CiPOX1 and CiPOX2. The amino acid sequences were compared and shown in the following Table 9. Further, for CINF_04670, nucleic acid was shown in SEQ ID NO. 4 and amino acid sequence was shown in SEQ ID NO. 5. Further, for CINF_13455, nucleic acid sequence was shown in SEQ ID NO. 6 and amino acid sequence was shown in SEQ ID NO. 7.

TABLE 9

| Section | CINF_04670(CiPOX1) | CINF_13455(CiPOX2) |
|---|---|---|
| Ct.POX4 | 43% | 40% |
| Ct.POX5 | 44% | 41% |
| Ct.POX2 | 42% | 41% |

SEQ ID NO. 4
(Nucleic acid)
TAGTGTCATGAAGCCTTTCTTCACCCGCAAGTTCAACGACGACCCTGA

TCTCAGTGCTCTTGAGGAAGAGGAGGCCGAGGAGAACGAGTAA

SEQ ID NO. 5
(Amino acid)
MTKSLSTNPANDVVIDGKKYNTFTEPPKAMAAERAKASFPVREMTYYLDG

GEKVTEYNEAVWEQLERAPAFDNTDYYDVCGDHELLRARTLAKVGAIAEI

VTDGRSERDIQKVLSFVSVIDPGAMTRIGVHFGLFLNGVRGSGTSEQFNY

WVGEGAANLSNFFGCFCMTELGHGSNVAGVETTATFDRNTEEFVINTPTI

AASKWWIGGAAHTATHGLVFARLIVDGKDYGVKNFVVPLRDRNTWNLMPG

VSIGDIGKKMGRDGIDNGWVQFSNVRIPRLFMMMKYAKVSKDGKVTQPPL

AQLAYGALISGRVSMVYDSYTWARRFLTIAIRYACCRRQFSSSPGGLETK

-continued

LIDYTFHQRRLLPRLAYAYAMNAGSAELYKIYFAATDRLASTKPTDKEGL

QSAIDDVKELFSVSAGLKAFSTWGTAQIIDECRQACGGLGYSGYNGFGQG

YNDWVVQCTWEGDNNVLTLSAGRSLIQSGLAIRKGEHVGAAASYLKRELN

AKLNGRSLEDLNVLIDGWEHVSAVGISQAVDRYVELEKEGVSQTEAFERL

SQQRYDVTRVHTRMYLIKSFFENLKTASPALQPVLTDLALLFALWSIEID

ASVFLRYGFLEPKDISTITVLVNKYTGKVREQAIPLTDAFNQSDFVINAP

IGNYNGDVYNNYFAKTKAANPPINTHPPYYDSVMKPFFTRKFNDDPDLSA

LEEEEAEENE

SEQ ID NO. 6
(Nucleic acid)
CGCATTCTTCAAGCGCACTCCCTATGAGCAACCCAGGCTCGATGAGA

TTTAA

SEQ ID NO. 7
(Amino acid)
MKANNTASLLKDGKELNTFTRPASDMQAERDRTSFPVREMTHFFNNGKEN

TEFLEKLFERIQRDPAFNNKDFYDLDYKPLRQRTFEQIGRMWSYLDELGA

DSPLARRFLSPFGMINPSAQTRVSVHYGLFVSALRGQGTDKQYEFWKSQG

CLSLNRFYGCFGMTELGHGSNVAELETTATFDRATDEFIIHTPNTAATKW

WIGGAAHSSNHTVCFARLIVDGKDYGVRNFVVPLRDPESHNLLPGIAVGD

IGKKMGRDGIDNGWIQFSNVRIPRTYMLMRYSQVTPEGKVIEPPLAQLTY

GALINGRVAMAYDSWVWARRFLTIALRYAAVRRQFSSTEGREESKLLDYV

LHQRRLIPLLAQAIGIEAAATELYRLFDEVTHHQASLDTSDRKAVSDMVD

KTKELFSLSAGLKAFSTWATVDTIDECRQACGGLGYLSATGFGQGFDDWV

VNCTWEGDNNVLCLSAGRSLIQSGCKVLDGKHVTGAADYLGRIKTLRGKS

LASGDLRDPKVLVGAWESVAAQAVMDAAEAYKKLRARGVSDKAAFEELSI

DRFNIARLHTROFQIKALFRKIANANPSIQKVLTNVGLLFALWSIEKNGS

PFLQYGFLTSDDMNKVIDLVTFYCGEVRDQVIGITDSFNISDFFLNSPIG

NYDGNAYENLMDSVTERNVPGTPCPYQDAMNAFFKRTPYEQPRLDEI

Example 8: Selection of CiPOX1 Gene-Deficient Strain

Figure 17:
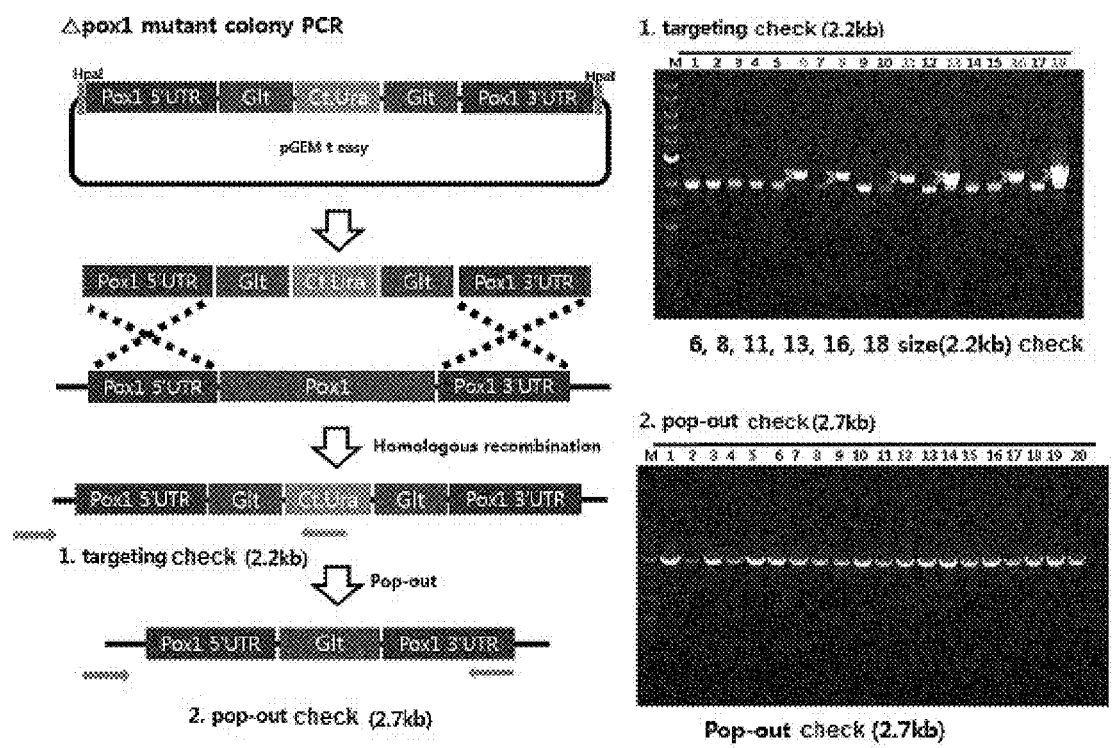
FIG. 17 is a mimetic diagram of a cassette for manufacturing a CiPOX1 gene-deficient strain and the result of gDNA PCR.

A CiPOX1 gene deletion cassette was manufactured using URA3 pop-out vector containing 500 bp homology region at both ends of the CiPOX1 gene, and then the CiPOX1 gene deletion cassette was introduced into the uracil auxotroph strain (Accession No.: KCTC13103BP) regulated in the S phase through transformation. The URA3 pop-out vector contains *Candida tropicalis* URA3 (Ct.URA3) gene for survival in the uracil-free medium and a repeated sequence derived from *Bacillus subtilis* at both ends of the Ct.URA3 gene for deletion (pop-out) of the Ct.URA3 gene, and the transformed strain can be selected on the uracil-free medium of Table 10 by the Ct.URA3 gene. SEQ ID NO. 8 shows the *Candida tropicalis* URA3 (Ct.URA3) sequence and SEQ ID NO. 9 shows the repeated sequence derived from *Bacillus subtilis*. Mimetic diagrams of the vector and the cassette and the results of confirming the sequence using gDNA PCR were shown in FIG. 17 (Accession No.: KCTC13104BP).

TABLE 10

| Medium composition | g/L |
| --- | --- |
| Dextrose | 20 |
| YNB without amino acid | 6.7 |
| Agar | 20 |

SEQ ID NO. 8
cgggacatgggggtagagaagaagggtttgattggatcatcatgacgcc tggtgtggggttggatgataaaggcgatgcgttgggccagcagtatagga ctgttgatgaggtggttctgactggtaccgatgtgattattgtcgggaga gggttgtttggaaaaggaagagaccctgaggtggagggaaagagatacag ggatgctggatggaaggcatacttgaagagaactggtcagttagaataaa tattgtaataaataggtctatatacatacactaagcttctaggacgtcat tgtagtcttcgaagttgtctgctagtttagttctcatgatttcgaaaacc aataacgcaatggatgtagcagggatggtggttagtgcgttcctgacaaa cccagagtacgccgcctcaaaccacgtcacattcgcctttgcttcatcc gcatcacttgcttgaaggtatccacgtacgagttgtaatacaccttgaag aacggcttcgtctgacccttgagcttcgcctcgttgtaatgattatacac atccaacgcttccaacctcgataaatggatcttctgcacttttgaaatcg ggtactggatcgcaagcaacgagaacgccgccgatgctccggcaagcaac acaaacgaggacttcaagatc SEQ ID NO. 9
gtttaatactggttttcggagaagcgcctgtacctccgtcatagccgctg atcacaatgacatctgcagtcgctttggcaacacctgcagcgattgttcc tacacctgcttttgacaccagctttacgctgattcttgcgtcacggttgg cattttcaaatcgtggatcagctgggctaaatcctcaatcgaataaatg tcatggtgtggcggaggtgagattaatccgacacctggcgttgacccacg gacatcggcaacccatggatataccttgttgccaggaagctgcccgcctt caccggcttagcaccttgagccattttaatctgcagctcatcagcattg acgaggtaatggcttttgacaccaaaccgtccggatgcaatttgtttgat cgcacttcttctatcatcgccgttctcatctggaacaaagcgtttgggat cttctccgccttcaccgctgttgcttttcctccaagacggttcattgcg attgctaaagcttcgt

Example 9: Selection of CiPOX2 Gene-Deficient Strain

Figure 18:
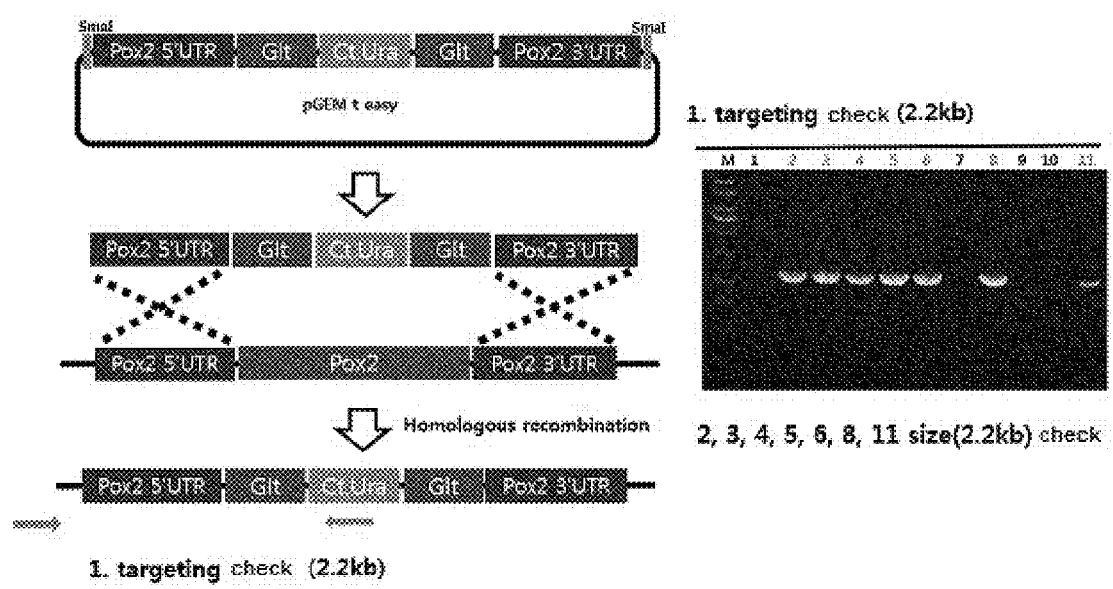
FIG. 18 is a mimetic diagram of a cassette for manufacturing a CiPOX2 gene-deficient strain and the result of gDNA PCR.

A CiPOX2 gene deletion cassette was manufactured using URA3 pop-out vector containing 500 bp homology region at both ends of the CiPOX2 gene, and then the CiPOX2 gene deletion cassette was introduced into the uracil auxotroph strain (Accession No.: KCTC13103BP) regulated in the S phase through transformation. The URA3 pop-out vector contains *Candida tropicalis* URA3 (Ct.URA3) gene for survival in the uracil-free medium and a repeated sequence derived from *Bacillus subtilis* at both ends of the Ct.URA3 gene for deletion (pop-out) of the Ct.URA3 gene, and the transformed strain can be selected on uracil-free medium. Mimetic diagrams of the vector and the cassette and the results of confirming the sequence using gDNA PCR were shown in FIG. 18 (Accession No.: KCTC13105BP).

Example 10: Selection of CiPOX1 and CiPOX2 Gene-Deficient Strain

Figure 19:
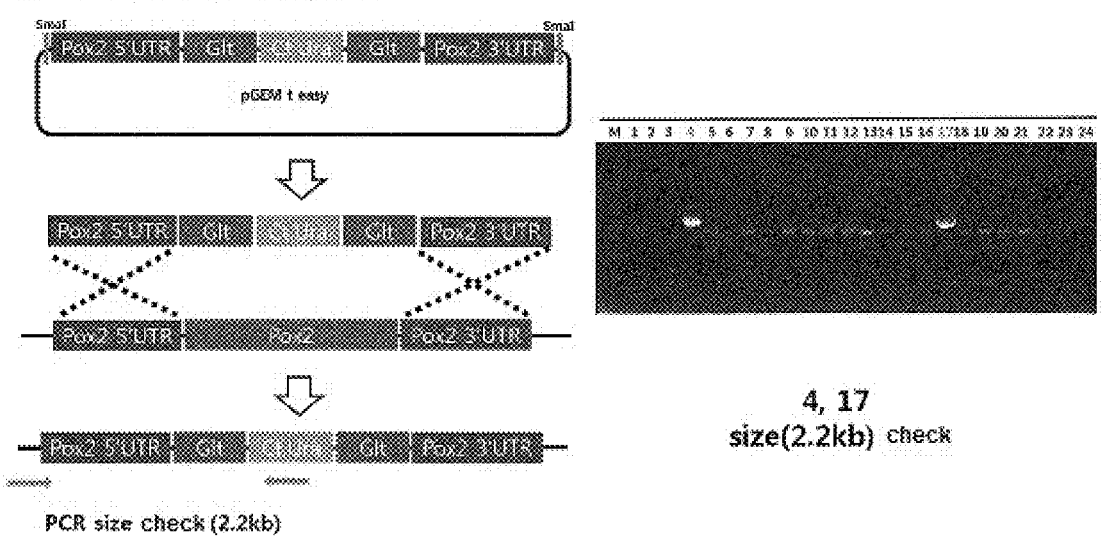
FIG. 19 is a mimetic diagram of a cassette for manufacturing a CiPOX1 and CiPOX2 genes-deficient strain and the result of gDNA PCR.

A CiPOX2 gene deletion cassette was manufactured using URA3 pop-out vector containing 500 bp homology region at both ends of the CiPOX2 gene, and then the CiPOX2 gene deletion cassette was introduced into a CiPOX1 and CtURA3 deficient strain regulated in the S phase through transformation. The CiPOX1 and CtURA3 deficient strain is manufactured by popping-out the Ct.URA3 from the CiPOX1 deficient strain (Accession No.: KCTC13104BP). The URA3 pop-out vector contains *Candida tropicalis* URA3 (Ct.URA3) gene for survival in the uracil-free medium and a repeated sequence derived from *Bacillus subtilis* at both ends of the Ct.URA3 gene for deletion (pop-out) of the Ct.URA3 gene. The transformed strain can be selected on uracil-free medium by the Ct.URA3 gene. Mimetic diagrams of the vector and the cassette and the results of confirming the sequence using gDNA PCR were shown in FIG. 19 (Accession No.: KCTC13106BP).

Figure 20:
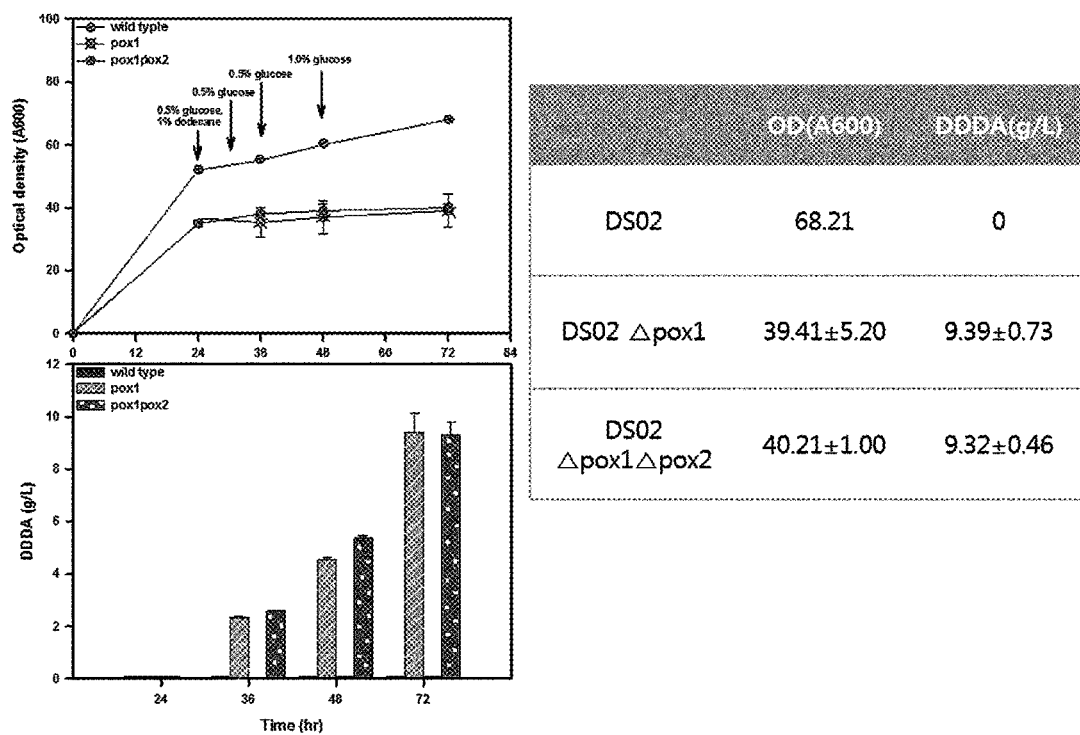
FIG. 20 is the result of showing capacity for producing dicarboxylic acid in a flask for a wild type strain, CiPOX1 gene-deficient strain, and CiPOX1/CiPOX2 genes-deficient strain.

Example 11: Flask Culture of *Candida infanticola* Transformant Strain for Dioic Acids Conversion In order to check dicarboxylic acid productivity of the transformant strain of the present invention, each of strains (wild type strain (Accession No.: KCTC 12820BP), POX1 gene deficient strain (Accession No.: KCTC13104BP), CiPOX2 gene deficient strain (Accession No.: KCTC13105BP), CiPOX1/CiPOX2 gene deficient strain (Accession No.: KCTC13106BP)) was flask cultured. 50 ml liquid culture was performed in a 500 ml baffled flask. The culture conditions were as follows: using YPED medium, total culture time of 72 hr, 30° C., 200 rpm, pH of 6 to 7.5. In order to ensure a sufficient amount of cell growth, the strain was cultured using glucose as a carbon source for 24 hr, and then dodecane 1% and potassium phosphate for adjusting to pH 7.5 were added thereto. From the addition of dodecane, 0.5% of glucose was added every 6 hr. As a result of confirming concentration of the converted dodecanedioic acid, at 72 hr, the concentration of the wild type strain (Accession No.: KCTC 12820BP) was 0 g/L, that of the POX1 gene-deficient strain (Accession No.: KCTC13104BP) was 9.39 g/L, and that of the POX1 and POX2 gene-deficient strain (Accession No.: KCTC13106BP) was 9.32 g/L. It was confirmed that the CiPOX1-deficient strain did not use the dodecane as a carbon source, and the dodecane was converted into dodecanedioic acid at 92% (mol/mol) or more. The results were shown in FIG. 20.

Example 12: 5 L Fermenter Culture of *Candida infanticola* Transformant Strain for Dioic Acids Conversion In order to check dicarboxylic acid productivity of the transformant strain of the present invention, 5 L-scale fermenter culture was performed using CiPOX1 and CiPOX2 gene-deficient strain (Accession No.: KCTC13106BP). The primary culture conditions were culture volume of 2 L, pH 5 to 6, temperature of 30° C., quantity of airflow of 1 v/v/m and agitation speed of 200 rpm. 10 N NaOH was used for pH adjustment, and as the dissolved oxygen in the culture solution decreased, rpm was controlled to maintain the dissolved oxygen at 30% or more. For the secondary culture for the conversion of dioic acids after 12 hr, time point of consumption of glucose for cell growth in the initial medium, 20 ml of dodecane as a ω-oxidation induction material for the secondary culture for dioic acids conversion was added, and glucose for providing reducing power was added at a rate of 4 g/hr. Culture conditions were changed to pH 7.5 and quantity of airflow of 0.5 v/v/m. After 12 hr of the secondary culture, methyl laurate as a substrate was added at a rate of 1.2 ml/hr to 1.5 ml/hr and culture for total 48 hr. It was confirmed that the converted dodecanedioic acids was produced at 17.64 g/L at 48 hr and the conversion yield was 90% (mol/mol) or more. The results were shown in FIG. 21.

Although specific embodiments of the present invention are described in detail as described above, it will be apparent to those skilled in the art that the specific description is merely desirable exemplary embodiment and should not be construed as limiting the scope of the present invention. Therefore, the substantial scope of the present invention is defined by the accompanying claims and equivalent thereof.

The invention claimed is:

1. A *Candida infanticola* strain producing dioic acids from a substrate containing hydrocarbons or fatty acids, selected from the group consisting of: mutant strain (*Candida infanticola* LC-DA01; KCTC13099BP), transformant strain (*Candida infanticola* KCTC13103BP, KCTC13104BP, KCTC13105BP, or KCTC13106BP), or a combination thereof.

2. The *Candida infanticola* strain according to claim 1, wherein the strain is *Candida infanticola* LC-DA01; KCTC13099BP.

3. The *Candida infanticola* strain according to claim 1, wherein the strain is KCTC13103BP.

4. The *Candida infanticola* strain according to claim 1, wherein the strain is KCTC13104BP.

5. The *Candida infanticola* strain according to claim 1, wherein the strain is KCTC13106BP.

* * * * *

UNITED STATES PATENT AND TRADEMARK OFFICE
CERTIFICATE OF CORRECTION

PATENT NO. : 10,604,775 B2
APPLICATION NO. : 15/762294
DATED : March 31, 2020
INVENTOR(S) : Shin et al.

It is certified that error appears in the above-identified patent and that said Letters Patent is hereby corrected as shown below:

In the Drawings

Figure 21:
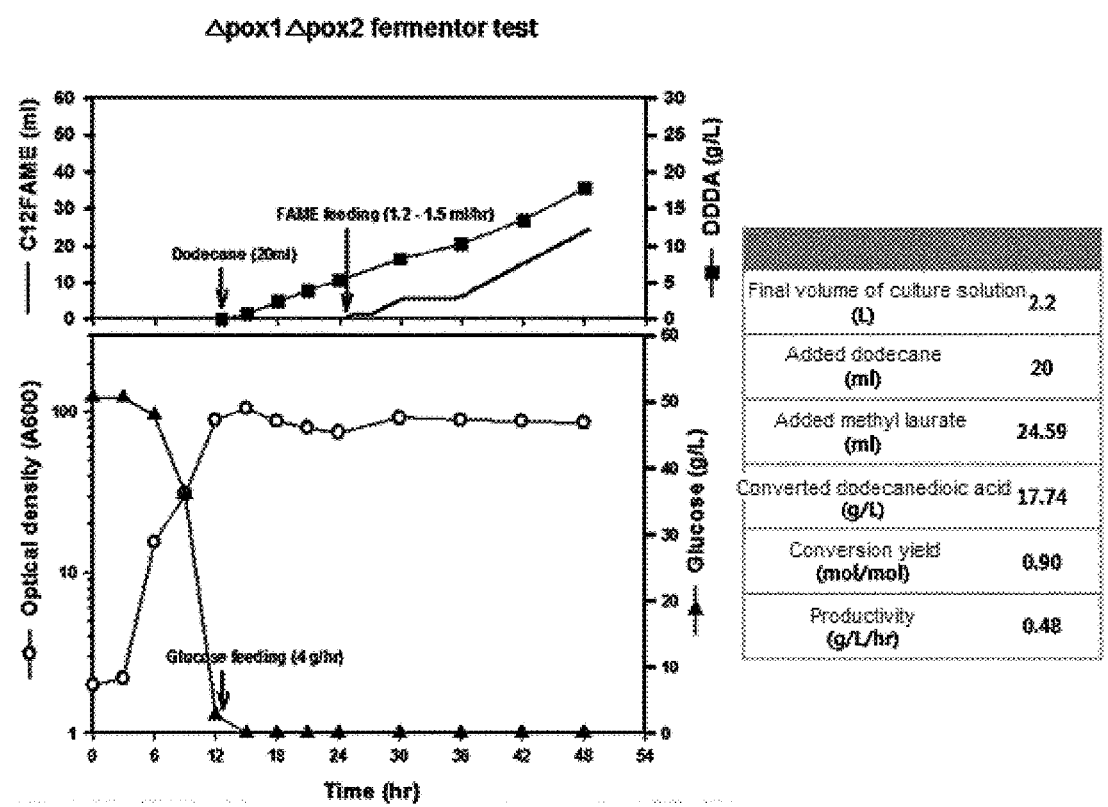
FIG. 21 is the result of showing capacity for producing dicarboxylic acid in a 5 L fermenter for a CiPOX1/CiPOX2 genes-deficient strain.

In sheet 21 of 21, FIG. 21, Line 1, delete "fermentor" and insert -- fermenter --.

In the Specification

In Column 3, Line 5, delete "DA01:" and insert -- DA01; --.

In Column 3, Line 47, delete "D502" and insert -- DS02 --.

In Column 3, Line 48, delete "D502" and insert -- DS02 --.

In Column 3, Line 49, delete "D502" and insert -- DS02 --.

In Column 3, Line 50, delete "D502" and insert -- DS02 --.

In Column 9, Lines 23-24, delete "infanficola DS02:" and insert -- infanticola DS02; --.

In Column 9, Line 25, delete "infanficola" and insert -- infanticola --.

In Column 10, Line 33, delete "O.D" and insert -- OD --.

In Column 13, Line 19, delete "122.5 g" and insert -- 122.5 --.

In Column 14, Line 15, delete "fluororotic" and insert -- fluoroorotic --.

In Column 15, Line 40, delete "O" and insert -- C --.

In Column 17, Line 11, delete "CtURA3" and insert -- Ct.URA3 --.

Signed and Sealed this
Thirteenth Day of October, 2020

Andrei Iancu
*Director of the United States Patent and Trademark Office*

CERTIFICATE OF CORRECTION (continued)
U.S. Pat. No. 10,604,775 B2

In Column 17, Line 12, delete "CtURA3" and insert -- Ct.URA3 --.

In Column 17, Line 31, delete "gene deficient" and insert -- gene-deficient --.

In Column 17, Line 32, delete "gene deficient" and insert -- gene-deficient --.

In Column 17, Line 33, delete "gene deficient" and insert -- gene-deficient --.

SEQUENCE LISTING

```
<160> NUMBER OF SEQ ID NOS: 9

<210> SEQ ID NO 1
<211> LENGTH: 434
<212> TYPE: DNA
<213> ORGANISM: Candida infanticola

<400> SEQUENCE: 1
tccgtaggtg aacctgcgga aggatcatta ttgagattca tattacacct gtgaaacaac      60
taaattgctt ggccgaaagg ccaatgtaac aaaaactatt ttacctatta tatctgaaaa     120
acgaaatcaa aagtttcaac aacggatctc ttggttctcg catcgatgaa gaacgcagca     180
aagcgcgata gttagtgtga attgcagacg tgaatcattg agtttttgaa cgcacattgc     240
accttctggt attccgggaa gtatacttgt gcgagcgtca tttcatcttc ataaagcaat     300
ttatgtgttg gggctgtagc cagccttgaa aaagatgata gagtacatgt tagacacaat     360
gtgcttttct atatttttga cctcgtatca agcaagatta cccgctgaac ttaagcatat     420
```

```
caataagcgg agga                                                       434
```

<210> SEQ ID NO 2
<211> LENGTH: 19
<212> TYPE: DNA
<213> ORGANISM: Candida infanticola

<400> SEQUENCE: 2

```
tccgtaggtg aacctgcgg                                                   19
```

<210> SEQ ID NO 3
<211> LENGTH: 20
<212> TYPE: DNA
<213> ORGANISM: Candida infanticola

<400> SEQUENCE: 3

```
tcctccgctt attgatatgc                                                  20
```

<210> SEQ ID NO 4
<211> LENGTH: 91
<212> TYPE: DNA
<213> ORGANISM: Candida infanticola

<400> SEQUENCE: 4

```
tagtgtcatg aagcctttct tcacccgcaa gttcaacgac gaccctgatc tcagtgctct      60
tgaggaagag gaggccgagg agaacgagta a                                     91
```

<210> SEQ ID NO 5
<211> LENGTH: 710
<212> TYPE: PRT
<213> ORGANISM: Candida infanticola

<400> SEQUENCE: 5

```
Met Thr Lys Ser Leu Ser Thr Asn Pro Ala Asn Asp Val Val Ile Asp
1               5                   10                  15

Gly Lys Lys Tyr Asn Thr Phe Thr Glu Pro Pro Lys Ala Met Ala Ala
            20                  25                  30

Glu Arg Ala Lys Ala Ser Phe Pro Val Arg Glu Met Thr Tyr Tyr Leu
        35                  40                  45

Asp Gly Gly Glu Lys Val Thr Glu Tyr Asn Glu Ala Val Trp Glu Gln
    50                  55                  60

Leu Glu Arg Ala Pro Ala Phe Asp Asn Thr Asp Tyr Tyr Asp Val Cys
65                  70                  75                  80

Gly Asp His Glu Leu Leu Arg Ala Arg Thr Leu Ala Lys Val Gly Ala
                85                  90                  95

Ile Ala Glu Ile Val Thr Asp Gly Arg Ser Glu Arg Asp Ile Gln Lys
            100                 105                 110

Val Leu Ser Phe Val Ser Val Ile Asp Pro Gly Ala Met Thr Arg Ile
        115                 120                 125

Gly Val His Phe Gly Leu Phe Leu Asn Gly Val Arg Gly Ser Gly Thr
    130                 135                 140

Ser Glu Gln Phe Asn Tyr Trp Val Gly Glu Gly Ala Ala Asn Leu Ser
145                 150                 155                 160

Asn Phe Phe Gly Cys Phe Cys Met Thr Glu Leu Gly His Gly Ser Asn
                165                 170                 175

Val Ala Gly Val Glu Thr Thr Ala Thr Phe Asp Arg Asn Thr Glu Glu
            180                 185                 190
```

-continued

Phe Val Ile Asn Thr Pro Thr Ile Ala Ala Ser Lys Trp Trp Ile Gly
            195                 200                 205

Gly Ala Ala His Thr Ala Thr His Gly Leu Val Phe Ala Arg Leu Ile
    210                 215                 220

Val Asp Gly Lys Asp Tyr Gly Val Lys Asn Phe Val Pro Leu Arg
225                 230                 235                 240

Asp Arg Asn Thr Trp Asn Leu Met Pro Gly Val Ser Ile Gly Asp Ile
                245                 250                 255

Gly Lys Lys Met Gly Arg Asp Gly Ile Asp Asn Gly Trp Val Gln Phe
            260                 265                 270

Ser Asn Val Arg Ile Pro Arg Leu Phe Met Met Met Lys Tyr Ala Lys
            275                 280                 285

Val Ser Lys Asp Gly Lys Val Thr Gln Pro Pro Leu Ala Gln Leu Ala
    290                 295                 300

Tyr Gly Ala Leu Ile Ser Gly Arg Val Ser Met Val Tyr Asp Ser Tyr
305                 310                 315                 320

Thr Trp Ala Arg Arg Phe Leu Thr Ile Ala Ile Arg Tyr Ala Cys Cys
                325                 330                 335

Arg Arg Gln Phe Ser Ser Pro Gly Gly Leu Glu Thr Lys Leu Ile
            340                 345                 350

Asp Tyr Thr Phe His Gln Arg Leu Leu Pro Arg Leu Ala Tyr Ala
            355                 360                 365

Tyr Ala Met Asn Ala Gly Ser Ala Glu Leu Tyr Lys Ile Tyr Phe Ala
    370                 375                 380

Ala Thr Asp Arg Leu Ala Ser Thr Lys Pro Thr Asp Lys Glu Gly Leu
385                 390                 395                 400

Gln Ser Ala Ile Asp Asp Val Lys Glu Leu Phe Ser Val Ser Ala Gly
                405                 410                 415

Leu Lys Ala Phe Ser Thr Trp Gly Thr Ala Gln Ile Ile Asp Glu Cys
            420                 425                 430

Arg Gln Ala Cys Gly Gly Leu Gly Tyr Ser Gly Tyr Asn Gly Phe Gly
            435                 440                 445

Gln Gly Tyr Asn Asp Trp Val Val Gln Cys Thr Trp Glu Gly Asp Asn
    450                 455                 460

Asn Val Leu Thr Leu Ser Ala Gly Arg Ser Leu Ile Gln Ser Gly Leu
465                 470                 475                 480

Ala Ile Arg Lys Gly Glu His Val Gly Ala Ala Ser Tyr Leu Lys
                485                 490                 495

Arg Glu Leu Asn Ala Lys Leu Asn Gly Arg Ser Leu Glu Asp Leu Asn
            500                 505                 510

Val Leu Ile Asp Gly Trp Glu His Val Ser Ala Val Gly Ile Ser Gln
            515                 520                 525

Ala Val Asp Arg Tyr Val Glu Leu Glu Lys Glu Gly Val Ser Gln Thr
    530                 535                 540

Glu Ala Phe Glu Arg Leu Ser Gln Gln Arg Tyr Asp Val Thr Arg Val
545                 550                 555                 560

His Thr Arg Met Tyr Leu Ile Lys Ser Phe Phe Glu Asn Leu Lys Thr
                565                 570                 575

Ala Ser Pro Ala Leu Gln Pro Val Leu Thr Asp Leu Ala Leu Leu Phe
            580                 585                 590

Ala Leu Trp Ser Ile Glu Ile Asp Ala Ser Val Phe Leu Arg Tyr Gly
            595                 600                 605

Phe Leu Glu Pro Lys Asp Ile Ser Thr Ile Thr Val Leu Val Asn Lys

```
              610                 615                 620
Tyr Thr Gly Lys Val Arg Glu Gln Ala Ile Pro Leu Thr Asp Ala Phe
625                 630                 635                 640

Asn Gln Ser Asp Phe Val Ile Asn Ala Pro Ile Gly Asn Tyr Asn Gly
                645                 650                 655

Asp Val Tyr Asn Asn Tyr Phe Ala Lys Thr Lys Ala Ala Asn Pro Pro
                660                 665                 670

Ile Asn Thr His Pro Pro Tyr Tyr Asp Ser Val Met Lys Pro Phe Phe
            675                 680                 685

Thr Arg Lys Phe Asn Asp Asp Pro Asp Leu Ser Ala Leu Glu Glu Glu
        690                 695                 700

Glu Ala Glu Glu Asn Glu
705                 710

<210> SEQ ID NO 6
<211> LENGTH: 52
<212> TYPE: DNA
<213> ORGANISM: Candida infanticola

<400> SEQUENCE: 6
cgcattcttc aagcgcactc cctatgagca acccaggctc gatgagattt aa            52

<210> SEQ ID NO 7
<211> LENGTH: 697
<212> TYPE: PRT
<213> ORGANISM: Candida infanticola

<400> SEQUENCE: 7

Met Lys Ala Asn Asn Thr Ala Ser Leu Leu Lys Asp Gly Lys Glu Leu
1               5                   10                  15

Asn Thr Phe Thr Arg Pro Ala Ser Asp Met Gln Ala Glu Arg Asp Arg
                20                  25                  30

Thr Ser Phe Pro Val Arg Glu Met Thr His Phe Phe Asn Asn Gly Lys
            35                  40                  45

Glu Asn Thr Glu Phe Leu Glu Lys Leu Phe Glu Arg Ile Gln Arg Asp
50                  55                  60

Pro Ala Phe Asn Asn Lys Asp Phe Tyr Asp Leu Asp Tyr Lys Pro Leu
65                  70                  75                  80

Arg Gln Arg Thr Phe Glu Gln Ile Gly Arg Met Trp Ser Tyr Leu Asp
                85                  90                  95

Glu Leu Gly Ala Asp Ser Pro Leu Ala Arg Arg Phe Leu Ser Pro Phe
            100                 105                 110

Gly Met Ile Asn Pro Ser Ala Gln Thr Arg Val Ser Val His Tyr Gly
        115                 120                 125

Leu Phe Val Ser Ala Leu Arg Gly Gln Gly Thr Asp Lys Gln Tyr Glu
    130                 135                 140

Phe Trp Lys Ser Gln Gly Cys Leu Ser Leu Asn Arg Phe Tyr Gly Cys
145                 150                 155                 160

Phe Gly Met Thr Glu Leu Gly His Gly Ser Asn Val Ala Glu Leu Glu
                165                 170                 175

Thr Thr Ala Thr Phe Asp Arg Ala Thr Asp Glu Phe Ile Ile His Thr
            180                 185                 190

Pro Asn Thr Ala Ala Thr Lys Trp Trp Ile Gly Gly Ala Ala His Ser
        195                 200                 205

Ser Asn His Thr Val Cys Phe Ala Arg Leu Ile Val Asp Gly Lys Asp
    210                 215                 220
```

```
Tyr Gly Val Arg Asn Phe Val Val Pro Leu Arg Asp Pro Glu Ser His
225                 230                 235                 240

Asn Leu Leu Pro Gly Ile Ala Val Gly Asp Ile Gly Lys Lys Met Gly
            245                 250                 255

Arg Asp Gly Ile Asp Asn Gly Trp Ile Gln Phe Ser Asn Val Arg Ile
                260                 265                 270

Pro Arg Thr Tyr Met Leu Met Arg Tyr Ser Gln Val Thr Pro Glu Gly
        275                 280                 285

Lys Val Ile Glu Pro Pro Leu Ala Gln Leu Thr Tyr Gly Ala Leu Ile
        290                 295                 300

Asn Gly Arg Val Ala Met Ala Tyr Asp Ser Trp Val Trp Ala Arg Arg
305                 310                 315                 320

Phe Leu Thr Ile Ala Leu Arg Tyr Ala Ala Val Arg Arg Gln Phe Ser
                325                 330                 335

Ser Thr Glu Gly Arg Glu Ser Lys Leu Leu Asp Tyr Val Leu His
                340                 345                 350

Gln Arg Arg Leu Ile Pro Leu Ala Gln Ala Ile Gly Ile Glu Ala
            355                 360                 365

Ala Ala Thr Glu Leu Tyr Arg Leu Phe Asp Glu Val Thr His His Gln
370                 375                 380

Ala Ser Leu Asp Thr Ser Asp Arg Lys Ala Val Ser Asp Met Val Asp
385                 390                 395                 400

Lys Thr Lys Glu Leu Phe Ser Leu Ser Ala Gly Leu Lys Ala Phe Ser
                405                 410                 415

Thr Trp Ala Thr Val Asp Thr Ile Asp Glu Cys Arg Gln Ala Cys Gly
            420                 425                 430

Gly Leu Gly Tyr Leu Ser Ala Thr Gly Phe Gln Gly Phe Asp Asp
            435                 440                 445

Trp Val Val Asn Cys Thr Trp Glu Gly Asp Asn Asn Val Leu Cys Leu
    450                 455                 460

Ser Ala Gly Arg Ser Leu Ile Gln Ser Gly Cys Lys Val Leu Asp Gly
465                 470                 475                 480

Lys His Val Thr Gly Ala Ala Asp Tyr Leu Gly Arg Ile Lys Thr Leu
                485                 490                 495

Arg Gly Lys Ser Leu Ala Ser Gly Asp Leu Arg Asp Pro Lys Val Leu
                500                 505                 510

Val Gly Ala Trp Glu Ser Val Ala Ala Gln Ala Val Met Asp Ala Ala
            515                 520                 525

Glu Ala Tyr Lys Lys Leu Arg Ala Arg Gly Val Ser Asp Lys Ala Ala
530                 535                 540

Phe Glu Glu Leu Ser Ile Asp Arg Phe Asn Ile Ala Arg Leu His Thr
545                 550                 555                 560

Arg Cys Phe Gln Ile Lys Ala Leu Phe Arg Lys Ile Ala Asn Ala Asn
                565                 570                 575

Pro Ser Ile Gln Lys Val Leu Thr Asn Val Gly Leu Leu Phe Ala Leu
            580                 585                 590

Trp Ser Ile Glu Lys Asn Gly Ser Pro Phe Leu Gln Tyr Gly Phe Leu
        595                 600                 605

Thr Ser Asp Asp Met Asn Lys Val Ile Asp Leu Val Thr Phe Tyr Cys
        610                 615                 620

Gly Glu Val Arg Asp Gln Val Ile Gly Ile Thr Asp Ser Phe Asn Ile
625                 630                 635                 640
```

Ser Asp Phe Phe Leu Asn Ser Pro Ile Gly Asn Tyr Asp Gly Asn Ala
                645                 650                 655

Tyr Glu Asn Leu Met Asp Ser Val Thr Glu Arg Asn Val Pro Gly Thr
            660                 665                 670

Pro Cys Pro Tyr Gln Asp Ala Met Asn Ala Phe Phe Lys Arg Thr Pro
        675                 680                 685

Tyr Glu Gln Pro Arg Leu Asp Glu Ile
        690                 695

<210> SEQ ID NO 8
<211> LENGTH: 671
<212> TYPE: DNA
<213> ORGANISM: Candida tropicalis

<400> SEQUENCE: 8
cgggacatgg ggggtagaga agaagggttt gattggatca tcatgacgcc tggtgtgggg    60
ttggatgata aaggcgatgc gttgggccag cagtatagga ctgttgatga ggtggttctg   120
actggtaccg atgtgattat tgtcgggaga gggttgtttg gaaaaggaag agaccctgag   180
gtggagggaa agagatacag ggatgctgga tggaaggcat acttgaagag aactggtcag   240
ttagaataaa tattgtaata aataggtcta tatacataca ctaagcttct aggacgtcat   300
tgtagtcttc gaagttgtct gctagtttag ttctcatgat ttcgaaaacc aataacgcaa   360
tggatgtagc agggatggtg gttagtgcgt tcctgacaaa cccagagtac gccgcctcaa   420
accacgtcac attcgccctt tgcttcatcc gcatcacttg cttgaaggta tccacgtacg   480
agttgtaata caccttgaag aacggcttcg tctgacccct tgagcttcgcc tcgttgtaat   540 gattatacac atccaacgct tccaacctcg ataaatggat cttctgcact tttgaaatcg   600
ggtactggat cgcaagcaac gagaacgccg ccgatgctcc ggcaagcaac acaaacgagg   660
acttcaagat c                                                       671

<210> SEQ ID NO 9
<211> LENGTH: 516
<212> TYPE: DNA
<213> ORGANISM: Bacillus subtilis

<400> SEQUENCE: 9
gtttaatact ggttttcgga gaagcgcctg tacctccgtc atagccgctg atcacaatga    60
catctgcagt cgctttggca acacctgcag cgattgttcc tacacctgct tttgacacca   120
gctttacgct gattcttgcg tcacggttgg cattttttcaa atcgtggatc agctgggcta   180
aatcctcaat cgaataaatg tcatggtgtg gcggaggtga gattaatccg cacctggcg   240 ttgacccacg gacatcggca acccatggat ataccttgtt gccaggaagc tgcccgcctt   300
cacccggctt agcaccttga gccattttaa tctgcagctc atcagcattg acgaggtaat   360
ggcttttgac accaaaccgt ccggatgcaa tttgtttgat cgcacttctt ctatcatcgc   420
cgttctcatc tggaacaaag cgtttgggat cttctccgcc ttcaccgctg ttgctttttc   480
ctccaagacg gttcattgcg attgctaaag cttcgt                            516